United States Patent [19]
Lee et al.

[11] Patent Number: 6,153,322
[45] Date of Patent: Nov. 28, 2000

[54] METHODS FOR MAKING FLUORINATED SURFACE MODIFYING AGENTS, METHODS OF USING SAME AND PRODUCTS MADE USING SAME

[76] Inventors: T. Randall Lee, 7447 Cambridge #100, Houston, Tex. 77054; Nupur Garg, 4459 N. MacGregor Way, #226 W, Houston, Tex. 77004; Michael Graupe, 8282 Cambridge #115, Houston, Tex. 77054; Young Seok Shon, 8299 Cambridge #1106, Houston, Tex. 77054

[21] Appl. No.: 09/038,220

[22] Filed: Mar. 11, 1998

Related U.S. Application Data

[63] Continuation-in-part of application No. 08/818,334, Mar. 14, 1997, abandoned.

[51] Int. Cl.[7] .................................................. B32B 9/04
[52] U.S. Cl. .............................. 428/704; 568/65; 568/74
[58] Field of Search .............................. 568/61, 65, 74; 428/704

[56] References Cited

U.S. PATENT DOCUMENTS 3,088,849   5/1963   Friedlander .
3,257,407   6/1966   Brace .

FOREIGN PATENT DOCUMENTS

96/34697   11/1996   WIPO .

*Primary Examiner*—Erma Cameron
*Attorney, Agent, or Firm*—Robert W. Strozier

[57] ABSTRACT

The present invention discloses fluorocarbon-containing surface modifying agents having an ω-fluorocarbon-containing tail group and a head group for reacting or interacting with surfaces such as metal, non-metallic, ceramic, other inorganic oxide or organic surfaces, cost effective method for making the agents, methods for treating surfaces therewith, the treated surfaces and devices made therefrom.

20 Claims, 9 Drawing Sheets

METHODS FOR MAKING FLUORINATED SURFACE MODIFYING AGENTS, METHODS OF USING SAME AND PRODUCTS MADE USING SAME

RELATED APPLICATIONS

This application is a continuation-in-part of U.S. patent application Ser. No. 08/818,334, filed Mar. 14, 1997 to Lee, now abandoned.

BACKGROUND OF THE INVENTION

1. Field of the Invention

This invention relates to the surface modifying agents, surfaces treated with the agents and a method for making surface modifying agents that impart non-wettable, non-stick, friction reducing or other properties to surfaces such as metal, ceramic or other modifiable surfaces.

More particularly, the present invention relates to surface modifying agents, surfaces treated with the agents and a versatile, low cost method for making fluorocarbon-containing surface modifying agents having an ω-fluorocarbon-containing tail and an α-hydroxy, α-amino, α-phosphino, α-thiol or disulfide head formed by coupling an α-halo-fluorocarbon-containing compounds with an ω-alkenyl compound.

2. Description of the Related Art

The synthesis of specifically fluorinated long chain αω-functionalized hydrocarbons remains a challenging enterprise for interfacial scientists. The generation of organized thin films from these molecules offers the opportunity to study and manipulate fundamental properties of fluorinated interfaces, such as wetting, adhesion and tribology. The ability to control the identities of the αω-functionalities using organic synthesis permits atomic-level control over the structure and composition of interfaces formed from these molecules using self-assembly techniques. Organic synthesis thus provides a convenient tool for fine-tuning the interfacial properties.

Several methods have been utilized for the preparation of compounds having perfluorinated terminal segments.[1-6] Many approaches have been designed to yield target molecules containing a terminal $CF_3$ group.[7-16] A limited number of methods have, however, provided the opportunity to introduce fluorinated segments of differing lengths.

Brace, for example, investigated the radical addition of several iodoperfluorinates to allylacetate.[1,2] This approach was based on initial studies by Park and Lacher[17] and Moore,[18] which utilized ultraviolet light as the radical source. By employing an azo initiator, however, Brace was able to complete the reaction within a few hours compared to five days when using UV light. Brace and previous investigators[19,20] proposed that the reaction proceeded through the formation of a perfluoroalkyl radical that attacked the terminal carbon of the olefinic group. Reduction of the resultant fluorinated iodoacetate with zinc or $LiAlH_4$ provided a variety of perfluoroalkylated compounds in excellent yields.[2]

Cloux and Kovats modified the approach developed by Brace to include the addition of 2,2,2-trifluoroethyl iodide to terminal alkenes.[21]. 2,2,2-Trifluoroethyl iodide is a liquid and made handling the reaction easier than the reaction using gaseous trifluoromethyl iodide. The authors noted that microanalyses failed to give correct and reproducible results.

Several groups have shown that thiol-terminated reagents can be used to change the surface properties of metallic surfaces due to the strong interaction between the thiol moiety and the metal atoms of the surface.

Although radical coupling of ω-alkenyl acetates with α-halo-fluorinated hydrocarbons has been reported and thiol surface modifications have been reported, there is a need in the industry for a cost effective, high yield and versatile method for making fluorinated alkanethiols and/or disulfides and their precursors which can be used to modify surface characteristics, imparting non-wettable, non-stick or low friction surface coatings to the surfaces.

SUMMARY OF THE INVENTION

The present invention provides surface modifying agents that have fluorinated tail groups and surface reactive head groups. The surface modifying agents are used to coat metallic, ceramic or other surfaces to influence, change, augment or enhance the surface characteristics of the material.

This invention provides a method for making ω-fluorinated surface modifying agents as set forth below utilizing the following generalized synthetic scheme which includes the steps of:

a. contacting, in the presence of a radical initiator, at least one (X-halo-fluorocarbon-containing compound of Formula (I):

with at least one ω-alkenyl compound of Formula (II):

where:
  $R_f$ is a linear or branched fluorocarbon-containing group;
  X is a halogen other than F;
  Q is an $(R)_{ii}(E)_{jj}Z$ group where:
    R is a carbon-containing group;
    E is $NR^1$, O, $PR^1$ or S where $R^1$ is a carbon-containing group; and
    Z is a hydrogen atom or a CGG' group where:
  G is $NR^2$, O, $PR^2$ or S;
    G' is $R^2$, $NR^2{}_2$, $OR^2$, $PR^2{}_2$, or $SR^2$; and
    $R^2$ is the same or different and is a hydrogen atom or a carbon-containing group; and
    ii and jj are integers having the value of 0 or 1;
to produce an intermediate of Formula (A):

b. contacting the intermediate of Formula (A) with:
  i. a reducing agent when Q is other than a hydrogen atom; or
  ii. a REZ precursor compound when Q is a hydrogen atom, to form a surface modifying agents of Formula (III):

where the groups are as previously defined.
The method can further include the step of:
  c. contacting agents of Formula (III) where Q is REZ and Z is CGG' with an acid or a base to form agents of Formula (III) where Q is REH according to the following reaction Equation (1)

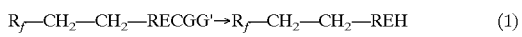

where the groups are as previously defined to form a preferred class of agents of Formula (III) where Z is a hydrogen atom.

The method of the present invention can further include the step of:

d. contacting the surface modifying agents of Formula (III) where Q is RZ (jj=0), Z is CGG' and G is oxygen and G' is $R^2$ or $OR^2$, with a reducing agent under appropriate reaction conditions to produce surface modifying agents of Formula (IV):

$$R_f-CH_2-CH_2-R-CH_2-OH \quad \text{(IV)}$$

where $R_f$ and R are as previously defined. Of course, the compounds of Formula (IV) can be converted into other agents of Formula (III) by standard chemical transformations by converting the alcohol into a good leaving group and then performing an appropriate displacement reaction with an appropriate nitrogen, phosphorus, or sulfur compound, generally, a nitrogen, phosphorus or sulfur base.

The present invention can also include an oxidization step or a second reduction step after the radical coupling step. The first reduction is designed to remove any olefinic moieties that might be present or formed in the preceding steps.

When Q is REZ, E is a sulfur atom and Z is a hydrogen atom, the present invention can also include an oxidation step where at least two agents of Formula (III) where E is S and Z is H are coupled to produce a coupled product of Formula (V):

$$R_f-CH_2-CH_2-REER'-CH_2-CH_2-R_f' \quad \text{(V)}$$

where $R_f$ and $R_f'$ and R and R' are the same or different groups as defined previously.

The present invention also provides methods for making the reagents of Formula (II), intermediates of Formula (A) and agents of general Formula (III).

The present invention further provides a preferred class of surface modifying agents of Formula (IIIa)

$$R_f-CH_2-CH_2-R-CGG' \quad \text{(IIIa)}$$

where $R_f$ and R are as previously defined and G is $PR^2$ or S and G' is $NR^2_2$, $OR^2$, $PR^2_2$ or $SR^2$, with G being S and G' being $NR^2_2$ or $SR^2$ preferred.

The present invention still further provides new surface modifying agents of Formula (VI):

$$(R_f)_\alpha-R''-(REZ)_\beta \quad \text{(VI)}$$

where $R_f$, R, E and Z are as previously described and where R" is a tetravalent atom such as carbon, silicon, germanium or the like, a double bond including a C=C double bond or hetero atom analogs thereof, e.g., C=N, C=Si, C=P, Si=Si, etc., a saturated, unsaturated, aromatic ring system or hetero containing saturated, unsaturated or aromatic ring system and where α and β are integers the sum of which does not exceed the maximum number of substituents R" can accommodate, e.g., if R" is C, Si or Ge, then α+β is ≦4, if R" is benzene, then α+β is ≦6, and if R" is C=C, then α+β is ≦4. The maximum number of substituents preferably means that α+β will be less than or equal to the number of normal or traditional bonding sites; however, hypervalent bonding such as pentavalent silicon, phosphorus, or sulfur, is included provided the resulting agents are stable enough for making surface modified substrates.

For R" representing a double bond, suitable agents include, without limitations, double bonds having at least one $R_f$ group and at least one REZ group attached to two different positions of the double bond. Preferred agents have two $R_f$ groups and two REZ groups for C=C, C=Si and Si=Si double bonds or two REZ group and one $R_f$ for C=N and C=P double bonds. For R" representing ring systems, at least one $R_f$ group is preferably in an opposed substitution arrangement with at least one REZ group such as 1-$R_f$-4-(REZ)-benzene, or 1,2-bis($R_f$)-4,5-bis(REZ) benzene, or the like. Preferred ring systems are aryl rings (aromatic rings) with 5 and 6 membered aromatic rings or rings having 6 π electrons being preferred. The present invention also provides methods for making the agents of Formula (VI), methods for treating surfaces therewith and treated surfaces having a partial or complete monolayer of agents of Formula (VI) thereon.

The present invention still further provides new surface modifying agents of Formula (VII):

$$R_f-R'''-REZ \quad \text{(VII)}$$

where $R_f$, E and Z are as previously described and where R''' is a crosslinkable group including an acetylenic group, a diacetylenic group, a polyacetylenic group, an alpha amino acid group, an alpha hydroxy acid group, a dialkoxysilenyl group, or the like. The present invention also contemplates bi-component systems of agents of Formula (VII) where one component is designed to react with the R''' group of the second components such as dihydroxy methylenes in combination with dicarboxy methylenes, diamino methylenes with dicarboxy methylenes, or similar bi-component systems. The present invention also provides methods for making the agents of Formula (VII), methods for treating surfaces therewith and treated surfaces having a partial or complete monolayer of agents of Formula (VII) thereon.

The present invention further provides surface modifying agents of the global Formula (VIII):

$$(R_f)_\alpha-\chi-(Q)_\beta \quad \text{(VIII)}$$

where $R_f$ and Q are as previously described and where χ is $CH_2$ $CH_2$, R" or R''' and α and β are integers the sum of which does not exceed the maximum number of substituents χ can accomodate.

This invention also provides a method for treating surfaces of substrates including contacting the substrate surface (s) with at least one agent of Formula (VIII) in an amount sufficient to form a partial or complete monolayer of the agent thereon. This invention also provides a method for treating surfaces including contacting a surface with an intermediate of Formula (A), an agent of Formulas (III–VII), mixtures or combinations thereof to form a partial or complete monolayer of the agent thereon.

The present invention also provides a substrate including a surface having a partial or complete monolayer formed of at least one agent of Formula (VIII). The present invention also provides a substrate including a surface having a partial or complete monolayer formed of an intermediate of Formula (A), an agent of Formulas (III–VII), mixtures or combination thereof. The present invention also provides devices incorporating a substrate including a surface having a partial or complete monolayer of at least one agent of Formula (VIII) or of an intermediate (A), an agent of Formulas (III–VII), mixtures or combination thereof. Devices include. without limitations, any device that has a surface that would perform better of its intended purpose if the surface was coated with a surface modifying agent to the present invention.

BRIEF DESCRIPTION OF DRAWINGS

The invention can be better understood with reference to the following detailed description together with the appended drawings in which like elements are numbered the same.

DESCRIPTION OF THE PREFERRED EMBODIMENTS

Figure 1:
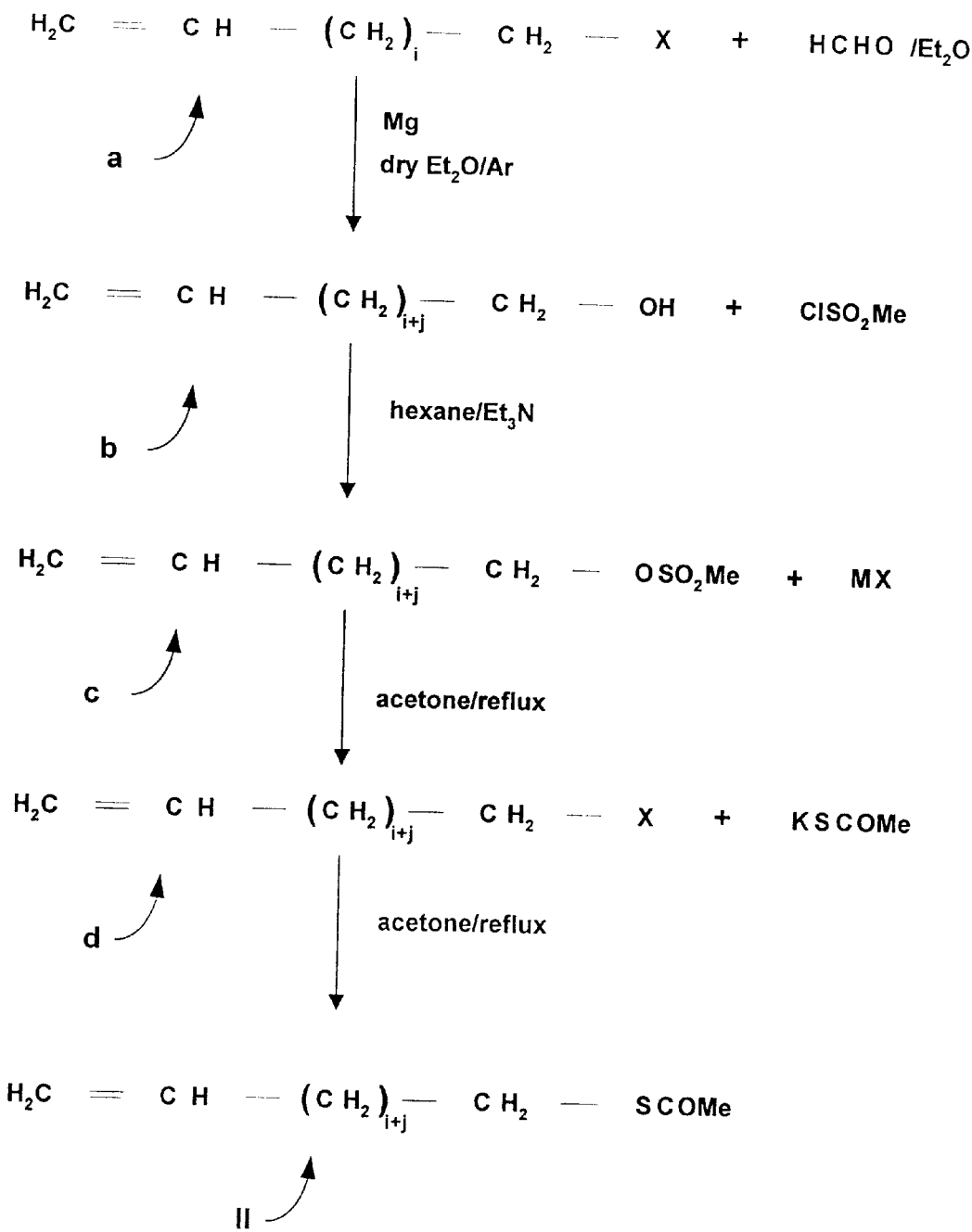
FIG. 1 is a synthetic scheme for the formation of ω-alkenyl compounds of Formula (II)
Figure 2:
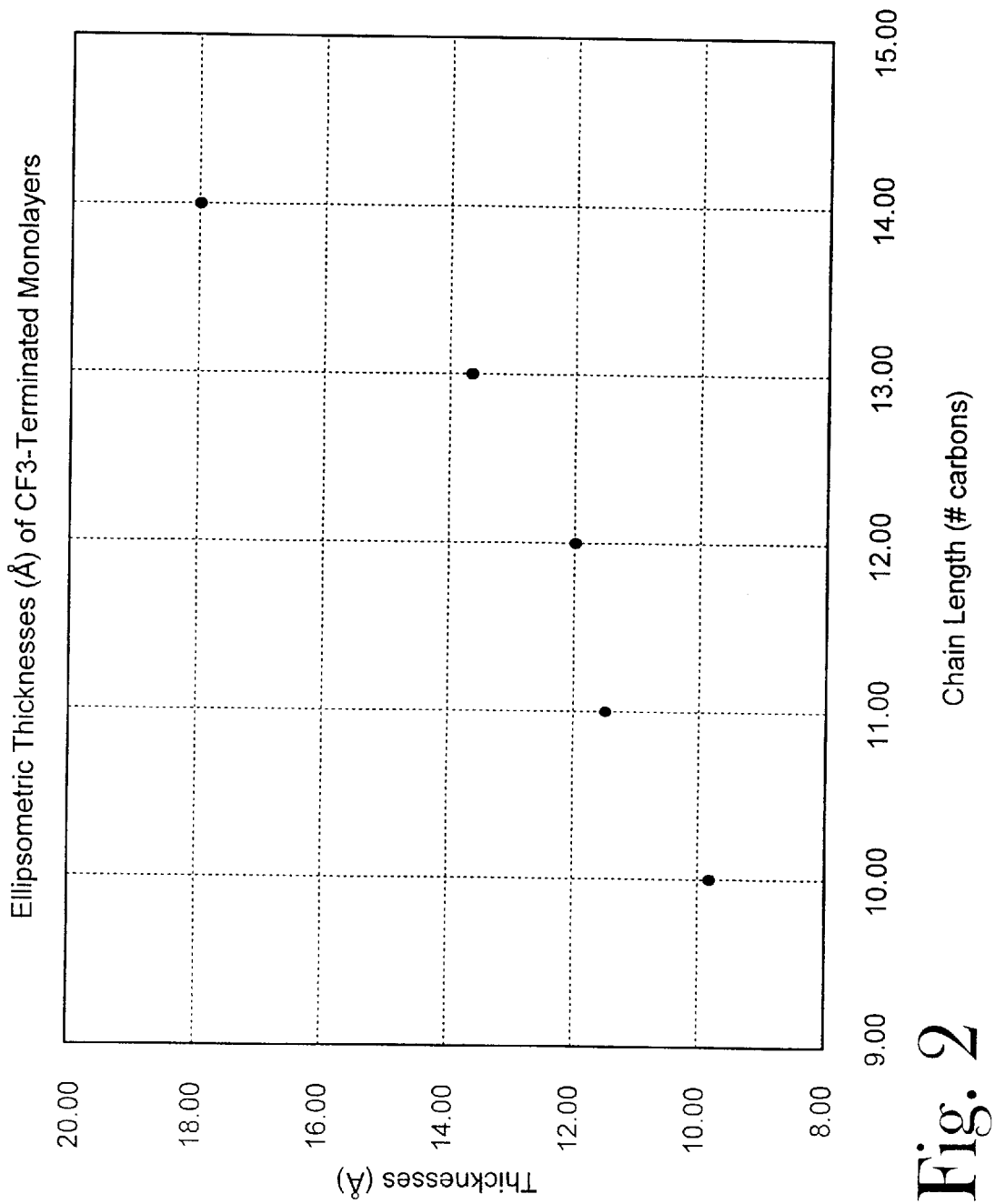
FIG. 2 is a plot of ellipsometric thickness measurements for a series of gold coated metallic surfaces treated with trifluoromethyl-terminated alkanethiol compounds of the present invention.
Figure 3:
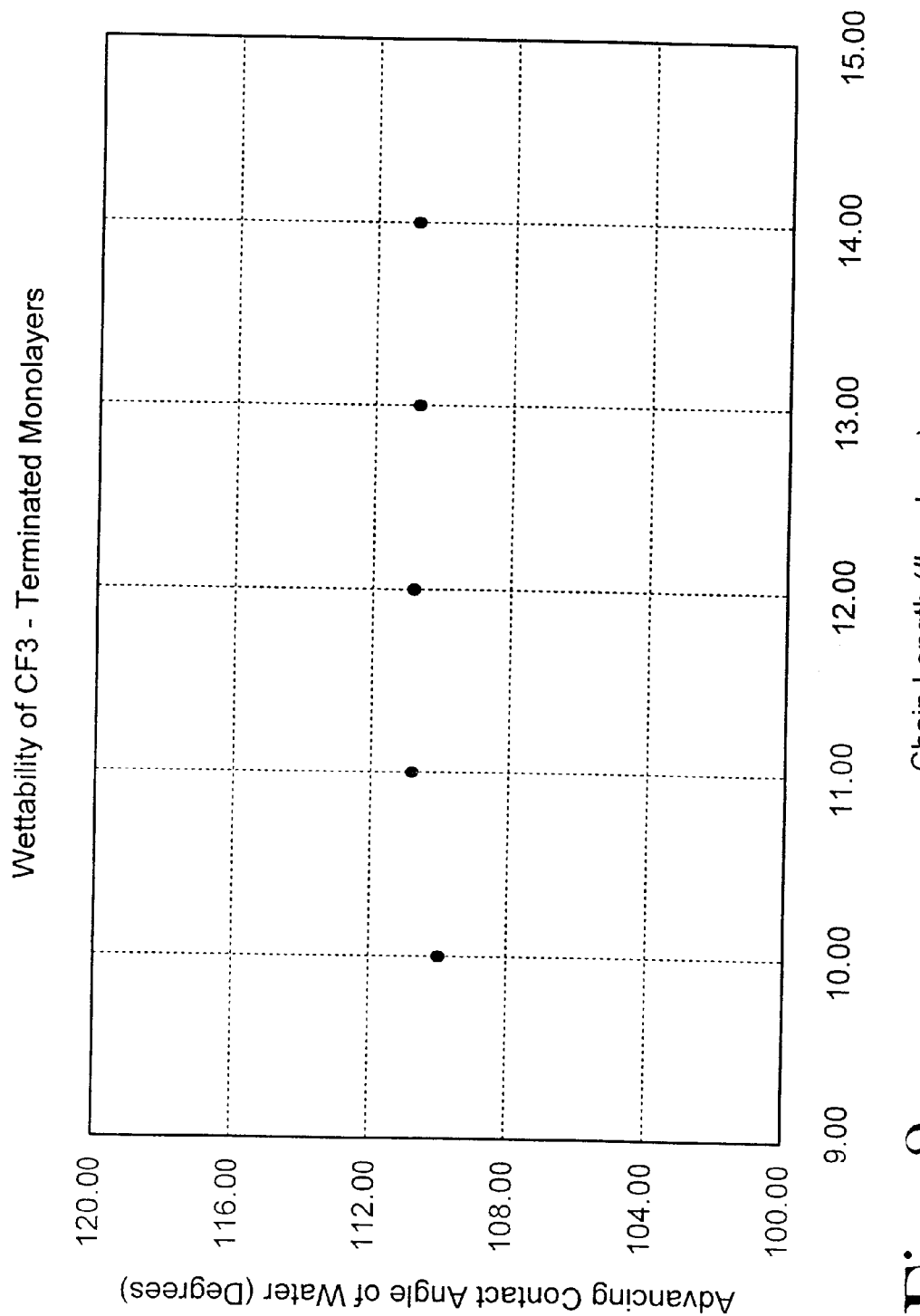
FIG. 3 is a plot of wettability data using water as the wetting agent for a series of gold coated metallic surfaces treated with trifluoromethyl-terminated alkanethiol compounds of the present invention.
Figure 4:
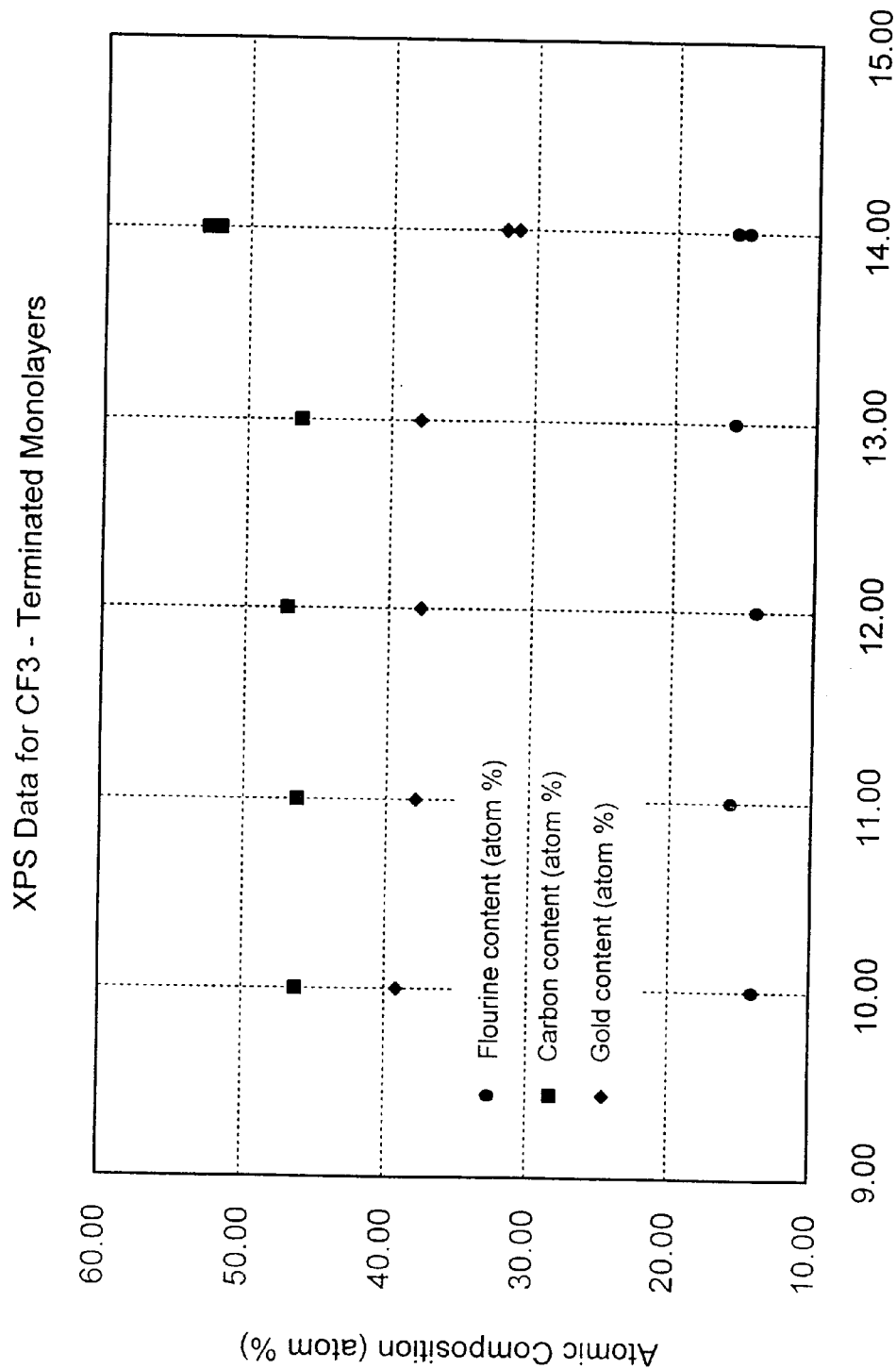
FIG. 4 is a plot of XPS data of the surface of a series of gold coated metallic surfaces treated with trifluoromethyl-terminated alkanethiol compounds of the present invention.

The inventors have found a low cost, highly effective and efficient synthetic method for preparing surface modifying agents having a fluorocarbon-containing tail group and a surface reactive head group. The head group or moiety contains at least one nitrogen atom, oxygen atom, phosphorus atom, or sulfur atom. The agents are designed to react with surfaces to form a partial or complete mono-molecular layer of the agents on the surface thereby modifying the surface characteristics. Because the tail part of the agent, the part extending away from the surface, is a fluorocarbon-containing group, the partial or complete mono-molecular layer (monolayer) generally imparts non-wettable, non-stick or low friction characteristics to the surface.

Although the surface modifying agents of the present invention generally react with the surfaces they are intended to treat, the exact nature of the reaction of the head groups of the agent with the surface will depend on the nature of the surface being treated and the nature of the agent. In certain circumstances, the exact nature of the bonding may not be well characterized or understood. Therefore, the inventors use the term reactive to include any interaction between the head groups of the agents and the surface that gives rise to monolayers on the surface that are stable for the intended purpose to which they are to be put. Generally, however, the nature of the interaction will be some type of physical or chemical absorption or adsorption mechanism and preferably the nature of the interaction or reaction of the head group with the surface will be a chemical bond such as a covalent, ionic, coordinate, hydrogen, a polar, mixtures and combinations thereof.

The method for making the surface modifying agents of Formulas (III–V) of the present invention generally involves the reaction of a compound of Formulas (I) and (II) in the presence of a radical initiator to produce an intermediate of Formula (A) according to Equation (2):

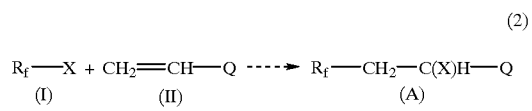

where: (a) $R_f$ is a fluorocarbon-containing group; (b) X is a halogen other than F; (c) Q is an $(R)_{ii}(E)_{jj}Z$ group where: (i) R is a carbon-containing group; (ii) E is $NR^1$, O, $PR^1$ or S where $R^1$ is a carbon-containing group; (iii) Z is a hydrogen atom or a CGG' group where: (1) G is $NR^2$, O, $PR^2$ or S; (2) G' is $R^2$, $NR^2_2$, $OR^2$, $PR^2_2$, or $SR^2$; and (3) $R^2$ is the same or different and is a hydrogen atom or a carbon-containing group; and (iv) ii and jj are integers having a value of 0 or 1.

The compounds of Formulas (I) and (II) are generally reacted together in a molar ratio between about 1:10 to about 10:1, with a ratio between about 1:5 and 5:1 being preferred and a ratio of between about 1:2 and 2:1 being particularly preferred. Because the reaction is bimolecular, the ratios of about 1:1 with 10% molar excess of either compound is especially preferred. Of course, other ratios can be used as well.

Although the exact ratio is not critical, the ratio may be adjusted so that one of the starting materials is substantially eliminated during the coupling reaction. If subsequent purification step are not commercially acceptable because of cost, then the coupling reaction of Equation (2) is generally run with an excess of $R_fX$, usually at least a 10% molar excess, so that substantially all of the reagents of Formula (II) are consumed. The substantial elimination of alkenyl reagents of Formula (II) as potential contaminants avoids complex separations in the final product.

Any alkenyl compounds remaining after the radical coupling and/or subsequent reduction can be easily removed through ozonolysis followed by chemical reduction or by hydrogenation to saturate the olefinic groups without causing problems to the Q groups or by reaction with 1,3-dipolar reagents such as nitrones to produce 1,3-dipolar addition adducts. which can be separated from the desired products by standard separation techniques that are well known in the art, e.g., HPLC, MPLC, GC, LC, or the like. Additionally, any internal olefins formed during the reduction of the intermediate of Formula (A) can be readily reduced by contacting the crude reaction product with a diimine based reducing reagents such as 2,4,6-triisopropyl benzene sulfonyl hydrazide, p-toluene sulfonyl hydrazide, or the like.

Next, when Q is not a hydrogen atom, the intermediate of Formula (A) can be to contacted with a reducing agent to remove the halogen X and form the surface modifying agents of Formula (III) according to Equation (3):

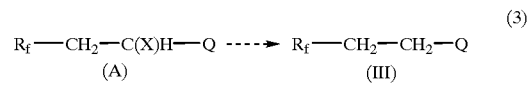

where the groups are as previously defined.

When Q=H (ii=jj=0 and Z=H), then the intermediates of Formula (A) can be contacted with an REH (Z=H) precursor reagent to form the surface modifying agents of Formula (III) where Q=REH. Moreover, when Q=HH, then the intermediates of Formula (A) can be directly converted to agents of Formula (IV) via an appropriate displacement reaction as is well-known in the art.

Although the agents of Formula (III) can be used directly as surface modifying agents, when Q is REZ, these agents are generally first converted, under either acid or base conditions in an appropriate solvent, to a preferred class of surface modifying agents of Formula (III) according to Equation (4):

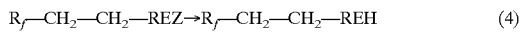
$$R_f\text{—}CH_2\text{—}CH_2\text{—}REZ \rightarrow R_f\text{—}CH_2\text{—}CH_2\text{—}REH \qquad (4)$$

where the groups are as previously defined. Preferably, the reaction of Equation (4) is carried out in the presence of an acid.

The reagents of Formula (III), especially when E is S, can also be coupled (even inadvertently) to form surface modifying agents of Formula (V) according to Equation (5):

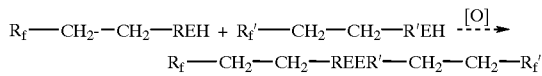
$$R_f\text{—}CH_2\text{—}CH_2\text{—}REH + R_f'\text{—}CH_2\text{—}CH_2\text{—}R'EH \xrightarrow{[O]}$$
$$R_f\text{—}CH_2\text{—}CH_2\text{—}REER'\text{—}CH_2\text{—}CH_2\text{—}R_f' \qquad (5)$$

where $R_f$ and $R_f'$ are the same or different and R and R' are the same or different and are as previously defined. Of course, this same process can occur when E is S or P giving rise to PP and mixed SP coupled agents.

In addition to the surface modifying agents of Formula (III–V), the present invention is also directed to surface modifying agents of Formula (VI–VII). The general synthetic schemes for agents of Formula (VI) are set forth in FIG. 5–8, while the general synthetic scheme for agents of Formula (VII) is set forth in FIG. 9.

Figure 5:
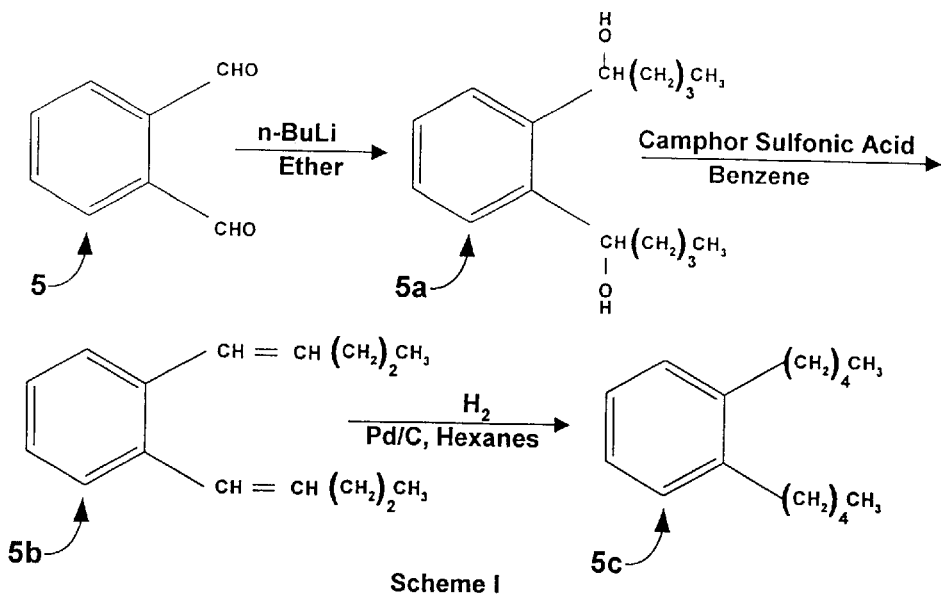
FIG. 5 is a chemical synthetic scheme for preparation of one class of surface modifying agents of the present invention.
Figure 5:
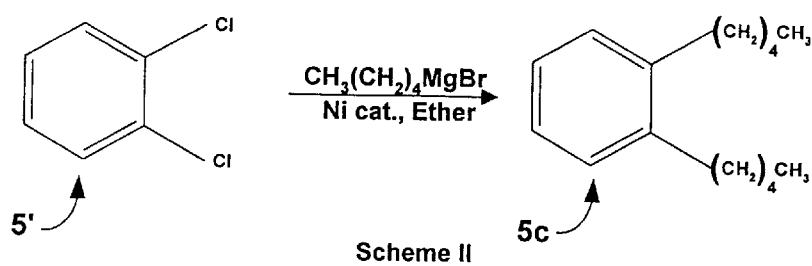
Figure 5:
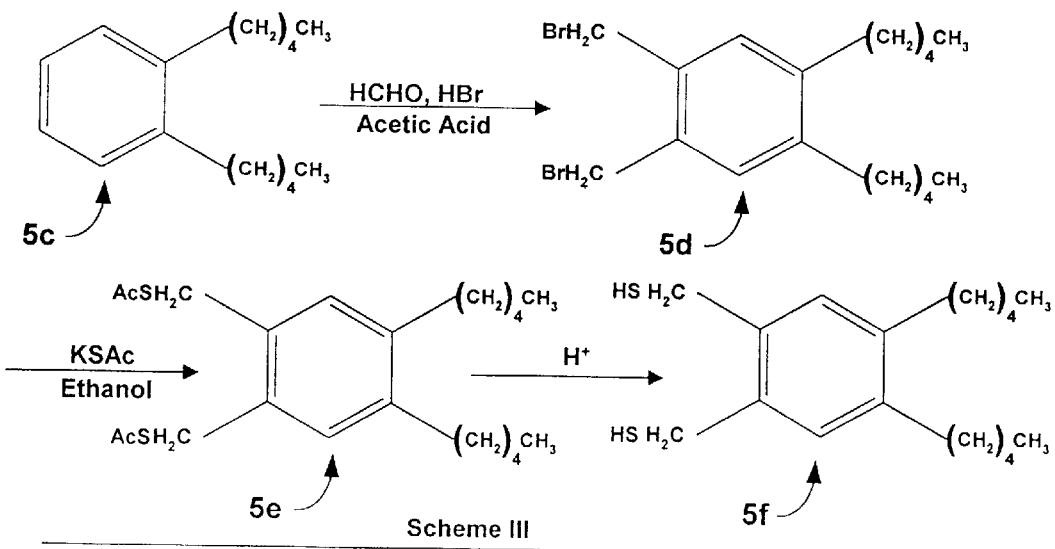

Referring to FIG. 5, a generalized synthetic scheme is shown for the formation of aromatic ring containing surface modifying agents of Formula (VIa), a preferred subclass of agents of Formula (VI):

$$(R^{70})_\alpha\text{—}R^\phi\text{—}(REZ)_\beta \qquad (VIa)$$

where: $R^{70}$ is a carbon-containing group, a fluorinated carbon-containing group or a fluorocarbon-containing group ($R_f$); $R^{100}$ is a ring system, preferably an aryl group, including, without limitation, a phenyl group or a hetero atom containing phenyl group, a naphthyl group, a polycondensed aromatic group or heterocyclic analogs thereof (preferably phenyl); REZ is as described above, but is preferably $CH_2EH$ where E is $NR^1$, O, $PR^1$ or S or $CH_3Si(OR^5)$ where $R^5$ is a carbon-containing group; and $\alpha$ and $\beta$ are integers having a sum no greater than the maximum number of substituents the $R_f$ group can accomodate. For phenyl, $\alpha+\beta$ cannot exceed 6 and preferably, a is between 1 and 3 and $\beta$ is between 1 and 3.

For aromatic rings with $\alpha$ and $\beta$ equal to 2, the synthetic scheme basically involves treating phthalaldehyde 5 with an alkyl lithium reagent. Although nBuLi is used in FIG. 5, it should be recognized that any alkyl lithium reagent including $R_f$Li can be used in place of nBuLi. Of course, the preparation of $R_f$Li is well known in the art and is generally achieved either by direct reaction with lithium metal or with an activated or unactivated alkyl lithium reagent. By activated, the inventors mean that the alkyl lithium reagent is coordinated to an amine or alkoxide modifier such as THF, tetramethylethylenediamine or the like.

This reaction yields a 1,2-di(alpha hydroxy alkyl)benzene 5a, which is then reacted with camphor sulfonic acid in a hydrocarbon solvent to yield the unsaturated analog 5b. Of course, other acids can be used as well. The unsaturated compound 5b can then be reduced using any standard reducing agents such as Pd on carbon to form the 1,2-dialkylbenzene 5c.

Alternatively, the 1,2-dialkyl benzene 5c can be prepared by the reaction of 1,2-dichlorobenzene with an appropriate Grignard reagent in the presence of a catalyst such as a Ni catalyst. The 1,2-dialkyl benzene 5c is then reacted with formaldehyde and hydrogen bromide in acetic acid to form a 1,2-bis(bromomethyl)-4,5-dialkyl benzene 5d which is then reacted with KSAc to form 5e followed by acid-catalyzed deprotection of the thiol group to yield 1,2-bis (mercaptomethyl)-4,5-dialkylbenzene 5f. This or an analogous synthesis can be used to prepare other aromatic surface modifying agents by using other displacement reactions to displace the bromomethyl (or chloromethyl) intermediate 5d such as hydroxide bases to form alcohols, reaction with lithium reagents followed by reaction with a silicon reagent to generate di-silyl surface modifying agents, or the like.

Figure 6:
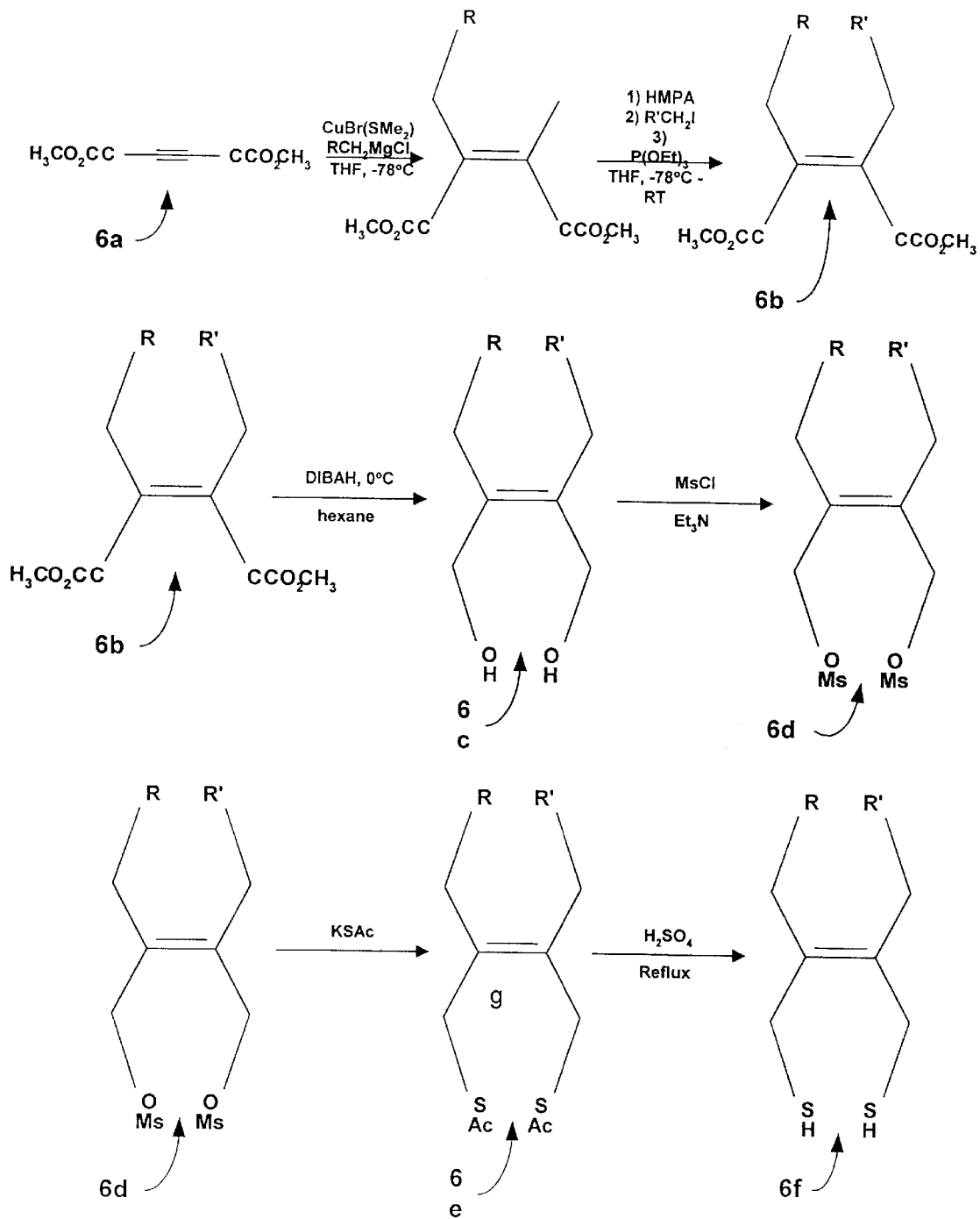
FIG. 6 is a chemical synthetic scheme for preparation of another class of surface modifying agents of the present invention.

Referring now to FIG. 6, a general synthetic procedure is shown for forming another preferred class of agents of Formula (VI) comprising cis and trans-2,3-dialkyl-1,4-dithiobutene surface modifying agents of Formula (VIb):

(VIb)

where: EZ is as described above, but is preferably EH where E is $NR^1$, O, $PR^1$ or S or $CH_3Si(OR^5)$ where $R^5$ is a carbon-containing group and $R^{86}$ is a carbon-containing group, a fluorinated carbon-containing group or a fluorocarbon-containing group $R_f$ as described previously. Of course, the carbon-carbon double bond can be replaced with a carbon-nitrogen double bond with the elimination of either one of the $CH_2R^\xi$ or $CH_2EZ$ groups, and preferably one of the $CH_2R^\xi$ groups.

For carbon—carbon double bonds with $\alpha=\beta=2$, the basic synthesis is shown in FIG. 6 and generally includes alkylation of an electron-deficient alkyne such as dimethyl acetylene dicarboxylate 6a using a Grignard reagent in the presence of a copper bromide-dimethylsulfide complex. This reaction forms a cis or trans-1,2-dicarboxymethyl-1-dialkyl, 2-copper ethene intermediate which is alkylated by an alkyl iodide reagent of general formula $R'CH_2I$ in the presence of HMPA and $P(OEt)_3$ in THF at –78° C. warming to RT (room temperature) to form intermediate 6b, a cis or trans-1,2-dicarboxymethyl-1,2-dialkyl ethene. Intermediate 6b is then reacted with a reducing agent which converts the carboxymethyl groups to hydroxymethyl groups to form intermediate 6c, a cis or trans-1,2-dihydroxymethyl-1,2-dialkyl ethene. The hydroxymethyl intermediate 6c is then reacted with mesyl chloride to form the mesylate 6d, which is reacted with KSAc to form intermediate 6e, a protected cis or trans-1,2-dithiol-1,2-dialkyl ethene. Intermediate 6e is then deprotected to yield the cis or trans-2,3-dialkyl-1,4-dithio butene 6f.

Figure 7:
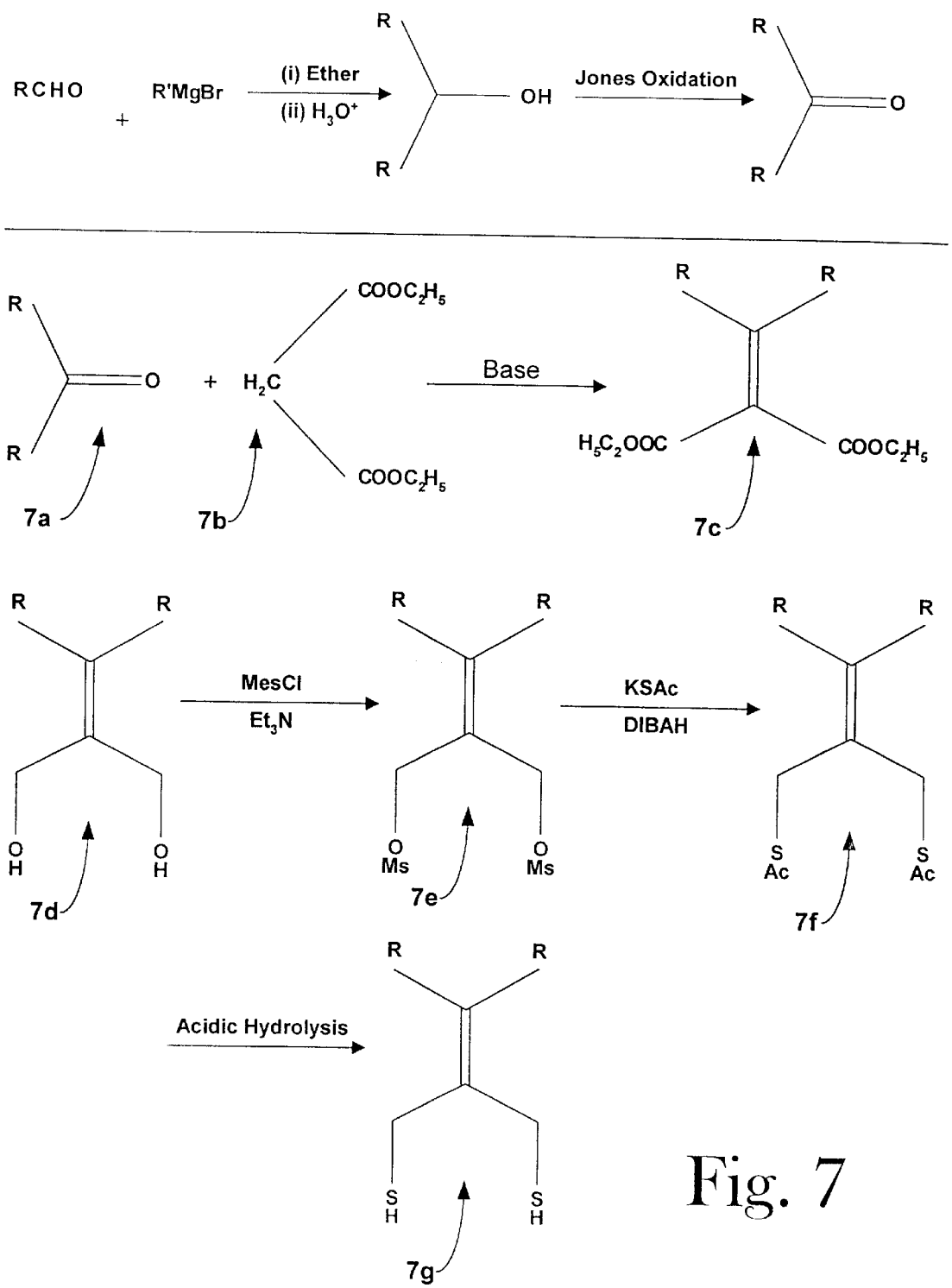
FIG. 7 is a chemical synthetic scheme for preparation of yet another class of surface modifying agents of the present invention.

Referring now to FIG. 7, a general synthetic procedure is shown for forming another preferred class of agents of Formula (VI) comprising 1,1-di(mercaptomethyl)-2,2-dialkyl ethene surface modifying agents of Formula (VIc):

(VIc)

where: EZ is described above, but is preferably EFH where E is $NR^1$, O, $PR^1$ or S or $CH_2Si(OR^5)$ where $R^5$ is a carbon-containing group and $R^\xi$ is a carbon-containing group, a fluorinated carbon-containing group or a fluorocarbon-containing group, $R_f$ as described previously. Of course, the carbon-carbon double bond can be replaced with a carbon-nitrogen double bond with the elimination of either one of the $CH_2R^\xi$ or $CH_2EZ$ groups, preferably one of the $CH_2R^\xi$ groups.

The synthetic scheme depicted in FIG. 7 basically involves the reaction of a ketone with an activated methylene compound such as diethyl malonate under basic conditions to form a carbon-carbon double bond containing reagent. Although ketones can be readily purchased, ketones can be prepared by reaction aldehydes with Grignard reagents followed by hydrolysis and oxidation of an intermediate dialkylhydroxylmethane sometimes called the Jones oxidation. Of course, any other ketone-forming reaction can also be used.

Referring back to FIG. 7, a ketone 7a is reacted with diethyl malonate 7b under basic conditions to form a 1,1-bis(ethylcarboxy)-2,2-dialkyl ethene 7c. Intermediate 7c is then reduced in DIBAH or another reducing agent to a 1,1-bis(hydroxymethyl)-2,2-dialkyl ethene 7d. The 1,1-bis(hydroxymethyl)-2,2-dialkyl ethene intermediate 7d is then reacted with mesyl chloride to form a mesylate 7e, which is reacted with KSAc to form intermediate 7f and deprotected under acidic conditions to form a 1,2-bis(mercaptomethyl)-2,2-dialkyl ethene 7g.

Figure 8:
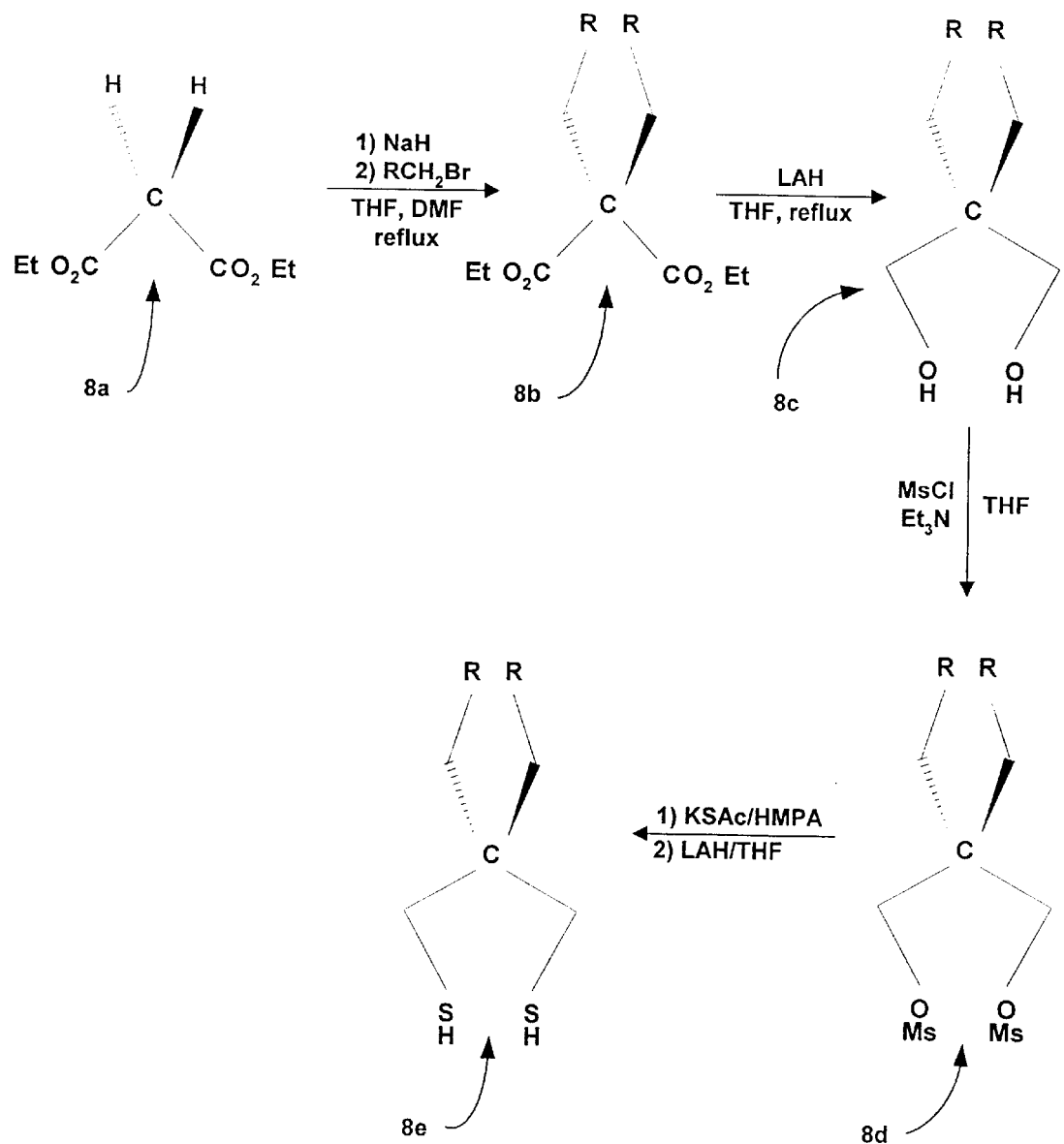
FIG. 8 is a chemical synthetic scheme for preparation of still another class of surface modifying agents of the present invention.

Referring now to FIG. 8, a general synthetic procedure is shown for forming another preferred class of agents of Formula (VI) comprising dimercaptoalkyldialkylmethane surface modifying of Formula (VId):

(VId)

where: E is as described above, but is preferably EH where E is $NR^1$, O, $PR^1$ or S or $Si(OR^5)$ where $R^5$ is a carbon-containing group and $R^\xi$ is a carbon-containing group, a fluorinated carbon-containing group or a fluorocarbon-containing group, $R_f$ as described previously.

The synthetic scheme of FIG. 8 generally involves reacting diethyl malonate 8a with an alkyl bromide in NaH to form a dialkyl dicarboxyethyl methane 8b. Intermediate 8b is then reduced with a reducing agent such as LAH (any other equivalent reducing agent can be used as well) to form a dialkyl di(hydroxymethyl) methane 8c. Intermediate 8c is then mesylated in the presence of triethylamine to form mesylated intermediate 8d. Intermediate 8d is then reacted with KSAc in the presence of HMPA and reduced in LAH in THF (any other equivalent reducing agent can be used as well) to form a dialkyl di(mercaptomethyl) methane 8e.

Figure 9:
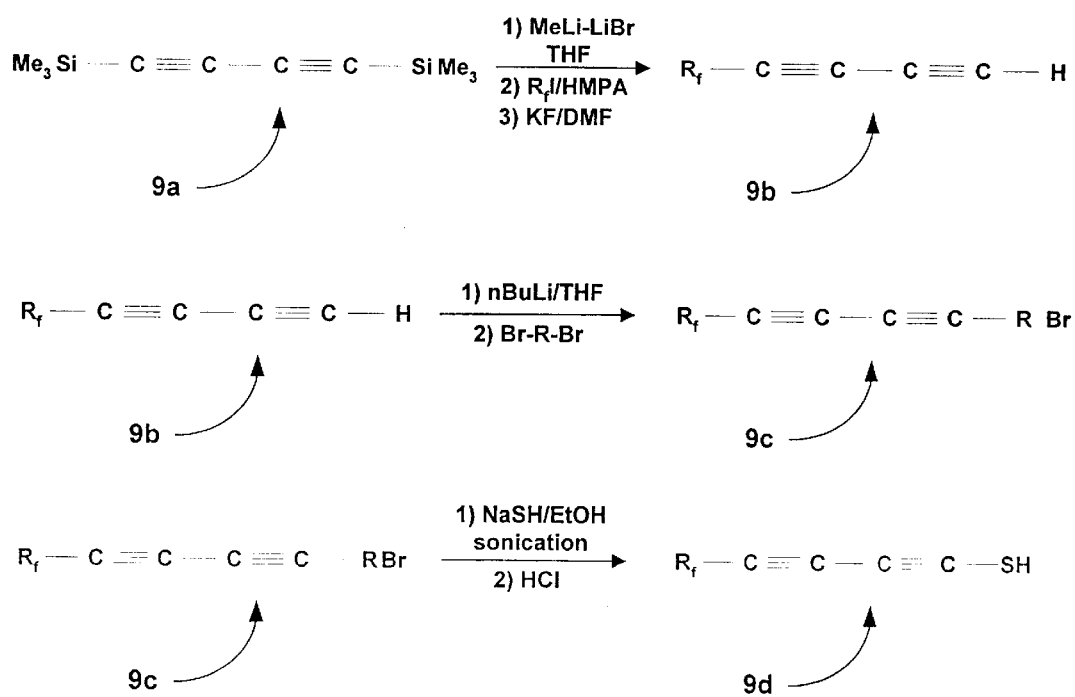
FIG. 9 is a chemical synthetic scheme for preparation of still another class of surface modifying agents of the present invention.

Referring to FIG. 9, a generalized synthetic procedure is set forth for forming a preferred class of surface modifying agents of Formula (VII), which are agents of Formula (VIIa):

(VIIa)

where $R_f$ is a fluorocarbon-containing group as previously described and REH is a surface reactive group as previously described. Preferably in the agents of Formula (VIIa), $R_f$ is a -fluorocarbon group having the following general formula $CF_3(CF_2)_o(CH_2)_p$ where o is an integer having a value between 0 and about 30 and p is an integer having a value between 1 and about 50. Preferably o is between 1 and about 20, and particularly, between about 1 and about 18, especially between about 6 and about 17. Preferably, p is between and 1 and about 40, and particularly. p is between about 1 and about 35.

The general synthetic scheme depicted is FIG. 9 involves the reaction of bis(trimethylsilyl)diacetylene 9a with a MeLi—LiBr complex in THF. After addition of the MeLi—LiBr complex, $R_fX$ (X=I, Br or Cl) in the presence of HMPA is added to the reaction mixture followed by KR in DMF (dimethylformamide) resulting in the formation of intermediate 9b, $R_fC\equiv C—C\equiv C—H$. Intermediate 9b is then reacted with n-BuLi in THF followed by the addition of an α, ω-dibromoalkane to yield intermediate 9c $R_f—C\equiv C—C\equiv C—RBr$. Intermediate 9c is then reacted with NaSH in ethanol under sonication and worked up under acid conditions to yield crosslinkable surface modifying agents 9d of Formula (VIIa). Of course, intermediate 9c can be reacted with appropriate nitrogen, oxygen, silicon or phosphorus reagents to yield other crosslinkable surface modifying agents of Formula (VII).

Surfaces including metallic surfaces, non-metallic surfaces such as organic surfaces, inorganic surfaces, ceramic surfaces, ceramic fiber surfaces, organic fiber surfaces or inorganic fiber surfaces, or other similar modifiable surfaces can be modified with at least one agent of the global Formula (VIII), at least one intermediate of Formula (A), or at least one agent Formulas (III–VII) by contacting the surface with at least one of these agents.

When the surface is a metallic surface and Q is REZ, then the Q groups of the surface modifying agents react or interact with the metal atoms at or near the surface to form a partial or complete monolayer of the agent on the metallic surface. In the case of metallic surfaces, E and Z preferably contains N, O, P or S.

When the surface is a non-metallic surface, the REZ groups of the surface modifying agents react or interact with active sites on the surface to form a partial or complete monolayer of the agent on the non-metallic surface. In the case of non-metallic surfaces such as ceramic surface or other inorganic surfaces, E and Z preferably contains N, O, P, S or Si. In the case of organic surfaces or organic fiber surfaces, E and Z are selected to react with exposed reactive sites on the organic surface or fiber surface such as a COOH group, OH group, NH group or the like.

By surface, the inventor means atoms or sites directly on the surface and atoms or sites about 1 to about 10 atomic or molecular layers below the surface. Thus, the surface modifying agents can react or interact with atoms or sites directly on the surface or near the surface (slightly below the actual surface). An ordinary artisan should recognize that surfaces generally have holes, breaks, cracks, crevices or the like associated therewith and the surface modifying agents would be expected to react or interact anywhere on the surface or near the surface of any accessible site on surface. The inventors, therefore, are not limiting the reaction or interactions of the surface modifying agents of global Formula (VIII), intermediates of Formula (a) or agents of Formulas (III–V) to atoms or sites forming the interface between the surfaces of an object and their surroundings; provided, of course, that the $R_f$ group of the agents extends out from the "surface" of the modified object or material.

These treated surfaces with a partial or complete monolayer of surface modifying agents of Formulas (III–VIII) thereon can be used for any non-stick application, non-wetting application, corrosion inhibiting application, and/or friction reducing application. Because the surface modifying agents of Formulas (III–VIII) have an $R_f$ moiety associated with the end of the agent not bound to the surface and because such $R_f$ moieties are known to reduce attractive chemical and physical interactions, the partial or complete monolayers impart a non-stick, non-wettable, low friction coating which is essential in improving flow characteristics of materials over the treated surfaces, in reducing friction between objects that contact the treated surface, in improving corrosion resistance of treated surfaces, or in reducing potential build up of the material on the treated surfaces.

These treated surfaces will generally result in contact angles with deionized water of between about 80° and about 180°, with angles between about 100° and about 150° being particularly preferred and angles between about 1100 and about 130° being especially preferred. Of course, certain of these surfaces can have contact angles approaching 180°for rough, amorphous surfaces, i.e., the water forms bead on the surface.

Device surfaces can be treated directly with one or more agents of Formulas (III–VIII) or intermediate of Formula (A). In the case of metal surfaces that form stable oxides, the surface is preferably treated when the surface is substantially free of surface oxides, which tend to reduce the efficiency of surface modification. Maintaining an oxide-free surface can be difficult requiring that the surface modifying agents be applied in an inert atmosphere such as by dipping the oxide-free surface in the agents neat or in an appropriate solvent. The surface modifying agents can also be sprayed onto the surface, vapor deposited onto the surface or applied in any other way commonly known in the art.

Alternately, for metals that form stable oxides or for any other type of surface, the surface to be treated can be coated with a metal that does not form a stable oxide such as gold. Gold-coated surfaces can then be contacted with at least one surface modifying agent 15 of Formulas (III-VIII) or intermediate of Formula (A) to impart a non-stick, low friction partial or complete monolayer of the agent(s) on the gold-coated surface. For most non-metallic surface, the appropriate agents, those that will react and interact strongly with active sites on the surface, can simply be brought in contact with the surface, either neat or in an appropriate solvent, by any method well-known in the art, including dipping, spraying, vapor depositing, washing, or the like.

The treating of a surface with at least one agent of Formulas (III–VIII) or intermediate of Formula (A) can generally be performed by contacting the surface with a millimolar solution of the agent in an appropriate solvent. The step of contacting can include dipping, spraying, vapor depositing, soaking, washing, or any other similar method for bringing the surface into contact with the modifying agents. Additionally, the amount of agents used are sufficient of achieve the desired surface coverage. Preferably, an excess of agent is used to insure complete monolayer formation.

Suitable solvents for treating surfaces with the agents of Formula (III–VIII) or intermediates of Formula (A) include, without limitations, hydrocarbon solvents such as hexane, octane, isooctane or the like, chlorinated solvents such as methylene chloride, trichloroethane, or the like, alcohols such as methanol, ethanol, isopropanol, or the like or ethers such as diethylether, THF or the like. Of course, any solvent can be used provided that the solvent allows the surface modifying agent to react with the surface to be treated. Under this broad definition, slurries, emulsions, dispersions, solutions, or mixtures thereof can be used as the carrier in the surface treating step.

Generally, the ω-alkenyl compounds of Formula (II) where Q is REZ, E is S and Z is $COR^2$ are preferably prepared according to the synthetic scheme shown in FIG. 1. The scheme involves a set of reactions that result in the formation of ω-alkenyl compounds of Formula (II). The number of steps ofthe scheme that a given starting material will undergo will depend on the nature of the starting material and the type of compound of Formula (II) that is desired.

In the first reaction, an α-halo-ω-alkene of Formula (a), where X is Cl, Br, or I, is first reacted with formaldehyde in the presence of magnesium-turnings (the Grignard synthesis) in dry ether to form an α-hydroxy-ω-alkene of Formula (b) with a chain length extended by a single carbon atom, i.e., j=1 in the Figure. Although this reaction is shown to produce a single carbon extension using formaldehyde, other reagents can also lead to single carbon extensions or even multiple carbon extensions. Thus, carbon dioxide addition would also result in a single carbon atom extension, while ethylene oxide would result in a two carbon extension.

In the second reaction the α-hydroxy-ω-alkenes of Formula (b) can be converted into a thioester by reacting them with methylchlorosulfone, methanesulfonyl chloride or mesyl chloride in a hydrocarbon solvent such as hexane in the presence of triethylamine, or any other suitable base, at room temperature to form an ω-alkenyl-α-mesylate of Formula (c).

Although the mesylate can be directly converted to a thiol or any other sulfur-containing group by reaction with $H_2S$, $Na_2S$, Bunte salt, thioacetate, thiourea or the like, the mesylate is preferably converted to a thioacetate group in a two step process. In the first step, the mesylates of Formula (c) are refluxed in the presence of MX, where M is Li, Na. K, Rb or Cs and X is Cl, Br, or I, in a solvent such as acetone to produce an α-halo-ω-alkene of Formula (d). The α-halo-ω-alkene of Formula (d) is then reacted with potassium thioacetate (KSCOMe) in ethanol or another similar solvent under reflux and an inert atmosphere, to form an ω-alkenyl thioacetate of Formula (II) where Q is REZ, E is S and Z is COMe. Of course, the α-halo-ω-alkenes for Formulas (a) or (d) can be reacted with other sulfur-containing groups such as $H_2S$, $Na_2S$, Bunte salt, thiourea or other thioester including thioacetate to generate compounds of Formula (11).

As is apparent in the scheme, if a given α-halo-ω-alkene compound of Formula (a) or (d) is commercially available, then the commercial α-halo-ω-alkene can be directly converted to a corresponding reagent of Formula (II).

Of course, the synthetic approaches described in the scheme shown in FIG. 1 can be generalized to the use of other reagents than potassium thioacetate to form other classes of compounds of Formula (II). Thus, the oxygen, nitrogen and phosphorus versions of potassium thioacetate can be used to form the oxygen, nitrogen and phosphorus compounds of Formula (II) as well as other reagents can be used as well even silicon reagents to produce compounds of Formula (II) where E is a Si-containing group.

Preferred ω-alkenyls of Formula (II) are ω-alkenyls where Q is REZ, R is a $(CH_2)_p$ moiety, E is S or $PR^1$, and Z is $COR^2$ where p is an integer having a value between about 1 and about 30 and $R^1$ and $R^2$ are the same or different and are H or a carbon-containing group. Particularly preferred ω-alkenyls, are ω-alkenyls where p is between about 1 and about 24 and E is S, and ω-alkenyls where p is between about 1 and about 18 and E is S are especially preferred.

Although the compounds of global Formula (VIII) where Q contains only O or N typically do not form stable surface modifications on metallic surfaces as compared to compounds of Formula (VIII) where Q contains S or P. However, these former compounds can be easily converted into metallic surface modifying agents where Q is S or P using standard reactions well-known in the art.

Besides being organic surface, organic fiber surface, ceramic surface or ceramic fiber surface modifying agents, the agents of Formulas (III-VIII) or intermediates of Formula (A) where Z contains N or O may have application in other synthetic processes where fluorinated amines or alcohols could be used to augment the physical and chemical properties of desired products. The amine and oxidized S-containing or P-containing agents can be used to produce L-B films, surfactants, or the like. While the alcohols and amines can be used to terminate condensation polymers or the like.

Suitable radical initiators useful in the reaction of Equation (2) include, without limitation, azo initiators such as AIBN or the like, peroxides such as benzoylperoxide or the like, hydroperoxides such benzoylhydroperoxide or the like, ionizing radiation, or other radical initiators, or mixtures or combinations thereof.

Suitable $R_f$ groups include without limitation, any fluorocarbon-containing groups. These groups include, without limitation, fluorinated alkyl groups, fluorinated aryl groups, fluorinated ara alkyl groups, fluorinated alka aryl groups, fluorinated alkyl-alkylene oxide groups, fluorinated alkyl-alkylene amine groups, or other fluorinated groups including an alkyl moiety and a hetero atom containing moiety. Preferred, fluorinated alkyl, ara alkyl and alka aryl groups are described by the general formula $C_nF_iH_j$ where i+j is equal to one less than the maximum number of hydrogen atoms that would be needed to complete the bonding valence of the carbons atoms in the group and i>1, i.e., the group has at least one F atom associated therewith. The alkyl moiety can be linear or branched. If the fluorinated group is a fluorinated linear alkyl group, then i+j=2n–1 and i>1. Preferred fluorinated moieties include linear fluorinated alkyl moieties of the general formula $F(CF_2)_k(CH_2)_l$ where k is an integer having a value between 1 and 30 and l is an integer having a value between 0 and about 2. Preferably, k is an integer having a value between 5 about and about 20 and particularly between about 8 and about 18. When $R_f$ includes atoms other than carbon, hydrogen and fluorine, the other atoms generally should not be substantially susceptible to radical addition or abstraction reactions and are stable to chemical reduction under the conditions described in the preparation ofthe surface modifying agents of Formulas (III)–(V) as described herein.

It should be recognized that although preferred ranges for the fluorinated carbon-containing groups are given, the particular choice of k and 1 for the group will depend on the purpose to which the surface to be treated is to be put. In some applications, a short perfluorinated-head group could be used, while in other applications longer perfluorinated-head groups may be preferred.

Suitable R groups include, without limitation, linear or branched moieties of the general formula $(CH_2)_{pp}$, where pp is an integer having a value between about 1 and about 50, a branched alkenyl group, an alkenyl aryl group, an ara alkenyl group or the like. Preferred R groups include $(CH_2)_{pp}$ groups where pp is an integer having a value between about 1 and about 40. The R group can also include atoms other than carbon and hydrogen. Preferred groups including oxygen are groups including one or more methylene oxide or ethylene oxide moieties in the carbon chain. Alkylated amine groups in the carbon chain are also useful R groups. Such R groups including non-carbon atoms should also be substantially non-susceptible to radical addition or abstraction reactions. R is preferably a linear group to enhance the packing of the surface modifying agent on the treated surface.

Suitable $R^1$ and $R^2$ groups include, without limitation, alkyl groups, aryl groups, ara alkyl groups, alka aryl groups or the like. In fact, $R^1$ and $R^2$ can be any group that does not interfere with the reactions described above.

Suitable reducing agents for use in the present invention include, without limitation, borohydrides such as sodium borohydride, lithium triethyl borohydride, or the like, aluminohydrides such as lithium aluminum hydride or the like. Although boro and alumino hydrides are preferred, any other reducing agent that does not interfere with the indicated transformations can also be used.

Suitable deblocking agents include strong acids such as HCl, $H_2SO_4$, or the like and bases such as amines, alkoxides or carbonates. Of course, other acids or bases can be used.

The following examples are included to illustrate the synthetic methodology disclosed in the present invention and are not meant to be construed as a limitation to the synthetic method.

EXAMPLES

General Information

Nuclear magnetic resonance spectra ($^1$H and $^{13}$C NMR) were recorded on a GE-300 (300 MHZ) spectrometer using chloroform-d as the solvent. Chemical shifts are reported as δ in units of part per million downfield from tetramethylsilane (δ 0.0) using the residual solvent signal as an internal standard: δ 7.26 ($^1$H) and δ 77.0 triplet ($^{13}$C). All coupling constants are reported in units of Hertz. Reactions were monitored by thin layer chromatography (TLC) using Whatman F 254 precoated silica gel plates (0.25 mm thickness). EM silica gel (63–200 μm, 35–70 μm) and reagent grade solvents were used for column chromatography and medium pressure liquid chromatography (MPLC). Anhydrous solvents were dried by passing through activated alumina and degassed by the freeze-pump-thaw method immediately prior to use.

GRIGNARD REACTIONS

Example 1

This example illustrates the preparation of 8-nonen-1-ol using a Grignard addition reaction from 7-octen-1-bromide.

Step a

Magnesium turnings (1.50 g, 0.062 mole and 2.50 g, 0.094 mole, respectively) were placed in a flame-dried 250 mL flask, which was equipped with a reflux condenser an addition funnel. A mixture of 7-octen-1-bromide (10.0 g, 0.052 mole) in 40 mL diethyl ether (dry, degassed) was placed in an addition funnel. Approximately, 20 mL diethyl ether (dry, degassed) were added to the flask along with ca. 5 mL of the mixture in the addition funnel. In order to initiate the reaction. a few drops of 1,2-dibromoethane were added and the reaction mixture was heated gently until the diethyl ether started to reflux. Once the reaction commenced, heating was removed, the stirrer set in motion and sufficient diethyl ether (dry, degassed) added to cover the Mg turnings. The remainder of the contents of the additional funnel was added slowly in order to maintain a gentle reflux. After the addition was finished, the mixture was refluxed for 15 min to drive the reaction to completion. The process was carried out under a slow, but steady flow of argon.

Step b

After the reaction mixture was allowed to cool to room temperature, the dropping funnel was replaced by a gas inlet for adding HCHO. This gas inlet was connected to a flask containing 7.7 g of p-formaldehyde (0.26 mole). Before connecting the apparatus to the flask holding the Grignard-reagent, it was flame-dried and purged with argon. By heating the flask containing p-formaldehyde to ca. 180° C., p-formaldehyde decomposed to formaldehyde, which was carried into the stirred Grignard-reagent by the applied slow stream of argon. For completion of the reaction, stirring under argon was continued for 1 h. About 20 g of crushed ice were added to the reaction flask, and stirring was continued until decomposition was completed. The mixture was finally neutralized with concentrated HCl and the organic and aqueous layers were separated. The aqueous phase was extracted with diethyl ether, and the organic-phases were combined washed with water, and dried over $MgSO_4$. The solvent was removed by rotary evaporation. The crude reaction mixture was purified by column chromatography on silica gel (hexane/acetone=1/10, 5/1, 2/1) affording 4.8 g of 8-nonen-1-ol (64% yield). The final product had the following properties: $^1H$ NMR (300 MHZ, $CDCl_3$): δ 5.86–5.72 (m, 1H), 5.01–4.89 (m, 2H), 3.65 (t, J=7.3 Hz, 2H), 2.02 (m, 2H), 1.54 (m, 2H), 1.39–1.29 (m, 8H). $^{13}C$ NMR (75.5 MHZ, $CDCl_3$): δ 138.32, 113.70, 61.71, 33.39, 32.20, 28.99, 28.76, 28.51, 25.44.

Example 2

This example illustrates the preparation of 11-dodecen-1-ol using a Grignard addition reaction from 10-undecen-1-bromide.

The two step reaction scheme described in Example 1 was followed except that 2.50 g, 0.094 mole of magnesium-turnings were used and 20.0 g, 0.086 mole of 10-undecen-1-bromide were used. The synthesis afforded 6.0 g of 11-dodecen-1-ol (38% yield). The final product had the following properties: $^1H$ NMR (300 MHZ, $CDCl_3$): δ 5.87–5.72 (m, 1H), 5.01–4.90 (m, 2H), 3.63 (t, J=7.3 Hz, 2H), 2.03 (m, 2H), 1.56 (m, 2H), 1.40–1.29 (m, 14H). $^{13}C$ NMR (75.5 MHZ, $CDCl_3$): δ 138.71, 113.84, 62.15, 33.59, 32.44, 29.44, 29.39, 29.32 (2 peaks), 28.97, 28.74, 25.63.

MESYLATF FORMATION REACTIONS

Example 3

This example illustrates the preparation of 8-nonen-1-mesylate from 8-nonen-1-ol.

A solution of 0.064 mole of 8-nonen-1-ol and 0.19 mole of triethylamine (3 molar excess) in 100 mL of hexane was prepared. To the stirred solution, 0.13 mole of methanesulfonyl chloride (2 molar excess) was added dropwise over 5 min. After the addition was complete, stirring was continued for 2 h. Cold water was poured into the reaction mixture to destroy any excess methanesulfonyl chloride. The aqueous layer was separated from the organic layer, and was extracted with diethyl ether. The organic phases were combined and washed with dilute HC, $H_2O$, 5% $NaHCO_3$ and $H_2O$. The organic layer was dried over $MgSO_4$ and the solvent was removed by rotary evaporation. The respective reactions afforded 8-nonen-1-mesylate in 95% yield. The final product had the following properties: $^1H$ NMR (300 MHZ, $CDCl_3$): δ 5.86–5.72 (m, 1H), 5.02–4.91 (m, 2H), 4.23 (t, J=7.4 Hz, 2H), 2.97 (s, 2H), 2.05 (m, 2H), 1.80 (m, 2H), 1.39–1.27 (m, 8H). $^{13}C$ NMR (75.5 MHZ, $CDCl_3$): δ 138.33, 113.78, 69.85, 36.52, 33.19, 28.59, 28.35 (2 peaks), 28.23, 24.86.

Example 4

This example illustrates the preparation of 9-decen-1-mesylate from 9-decen-1-ol.

The procedure of Example 3 was followed except that 9-decen-1-ol was used. The procedure afforded 9-decen-1-mesylate in 96% yield having the following properties: $^1H$ NMR (300 MHZ, $CDCl_3$): δ 5.87–5.72 (m, 1H), 5.01–4.90 (m, 2H), 4.21 (t, J=7.4 Hz, 2H), 2.99 (s, 3H), 2.03 (m, 2H), 1.81 (m, 2H), 1.37–1.28 (m, 1OH). $^{13}C$ NMR (75.5 MHZ, $CDCl_3$): δ 138.62, 113.87, 69.98, 36.83, 33.40, 28.90, 28.77, 28.61 (2 peaks), 28.48, 25.05.

Example 5

This example illustrates the preparation of 11-dodecen-1-mesylate from 11-dodecen-1-ol.

The procedure of Example 3 was followed except that 11-dodecen-1-ol was used. The procedure afforded 11-dodecen-1-mesylate in 92% yield having the following properties: $^1H$ NMR (300 MHZ, $CDCl_3$): δ 5.88–5.74 (m, 1H), 5.03–4.93 (m, 2H), 4.24 (t, J=7.4 Hz, 2H), 2.98 (s, 3H), 2.05 (m, 211), 1.81 (m, 2H), 1.40–1.28 (m, 14H).

IODIDE FORMATION REACTIONS

Example 6

This example illustrates the preparation of 8-nonen-1-iodide from 8-nonen-1-mesylate.

0.243 mole of KI was dissolved in 250 mL of acetone. 0.081 mole of 8-nonen-1-mesylate was added dropwise to the stirred solution over 10 min. After the mixture cooled to room temperature, 100 mL of hexane was added to the stirred mixture. Addition of 100 ml of $H_2O$ dissolved the white precipitate ($KOSO_2CH_3$) formed during the reaction. The aqueous phase was separated from the organic phase and extracted with hexane. The organics phases were combined and washed with $H_2O$. The organic phase was dried over $MgSO_4$ and the solvent was removed by rotary evaporation. The respective reaction afforded 8-nonen-1-iodide in 99% yield. The final product had the following properties: $^1H$ NMR (300 MHZ, $CDCl_3$): δ 5.86–5.71 (m, 1H), 5.02–4.91 (m, 2H), 3.16 (t, J=7.4 Hz, 2H), 2.03 (m, 2H), 1.83 (m, 2H), 1.39–1.27 (m, 8H). $^{13}C$ NMR (75.5 MHZ, $CDCl_3$): δ 138.64, 114.11, 33.55, 33.35, 30.28, 28.70, 28.62, 28.22, and 6.93.

Example 7

This example illustrates the preparation of 9-decen-1-iodide from 9-decen-1-mesylate.

The procedure of Example 6 was followed except that 9-decen-1-mesylate was used.

The procedure afforded 9-decen-1-iodide in 99% yield having the following properties: $^1H$ NMR (300 MHZ, $CDCl_3$): δ 5.87–5.72 (m, 1H), 5.01–4.90 (m, 2H), 3.17 (t, J 7.4 Hz, 2H), 2.03 (m, 2H), 1.81 (m, 2H), 1.37–1.28 (m, 1OH). $^{13}C$ NMR (75.5 MHZ, $CDCl_3$): δ 138.90, 114.11, 33.73, 33.52, 30.44, 29.23, 28.97, 28.83, 28.46, 6.93.

Example 8

This example illustrates the preparation of 11-dodecen-1-iodide from 11-dodecen-1-mesylate.

The procedure of Example 6 was followed except that 11-dodecen-1-mesylate was used. The procedure afforded 11-dodecen-1-iodide in 99% yield having the following properties: $^1H$ NMR (300 MHZ, $CDCl_3$): δ 5.86–5.70 (m, 1H), 5.00–4.90 (m, 2H), 3.15 (t, J=7.4 Hz, 2H), 2.04 (m, 2H), 1.81 (m, 2H), 1.38–1.26 (m, 14H). $^{13}C$ NMR (75.5 MHZ, $CDCl_3$): δ 138.79, 114.02, 33.76, 33.56, 30.49, 29.42 (three peaks), 29.09, 28.90, 28.53, 6.53.

THIOACETATE FORMATION REACTIONS

Example 9

This example illustrates the preparation of 7-octen-1-thioacetate from 7-octen-1-iodide.

0.086 Mole of potassium thioacetate was dissolved in 100 mL of absolute ethanol (previously degassed) under argon. To the stirred solution, 0.043 mole of 7-octen-1-iodide was added dropwise over 10 min. Stirring was continued, and the mixture was heated to reflux for 6 h under argon. After the mixture cooled to room temperature, the precipitated KI was filtered off and rinsed with ethanol. The ethanol phases were combined, concentrated, and diluted with $H_2O$. The mixture was extracted with diethyl ether. The KI was dissolved in $H_2O$ and this mixture was also extracted with diethyl ether. The ether phases were combined, washed with $H_2O$, and dried over $MgSO_4$. The mixture was decolorized with Norit and the solvent was removed by rotary evaporation. The crude product was purified by column chromatography on silica gel (hexane/acetone=1/0, 10/1) affording 7-octen-1-thioacetate in 95% yield. The final product had the following properties: $^1H$ NMR (300 MHZ, $CDCl_3$): δ 5.90–5.73 (m, 1H), 5.03–4.91 (m, 2H), 2.86 (t, J=7.4 Hz, 2H), 2.33 (s, 3H), 2.02 (m, 2H), 1.55 (m, 2H), 1.40–1.29 (m, 6H). $^{13}C$ NMR (75.5 MHZ, $CDCl_3$): δ 193.69, 138.20, 113.76, 33.15, 29.76, 29.06, 28.34, 28.21, 28.11 (2 peaks).

Example 10

This example illustrates the preparation of 8-nonen-1-thioacetate from 8-nonen-1-iodide.

The procedure of Example 9 was followed except that 8-nonen-1-iodide was used. The procedure afforded 8-nonen-1-thioacetate in 91% yield having the following properties: $^1H$ NMR (300 MHZ, $CDCl_3$): 67 5.89–5.71 (m, 1H), 5.01–4.89 (m, 2H), 2.87 (t, J=7.4 Hz, 2H), 2.33 (s, 3H), 2.03 (m, 2H), 1.52 (m, 2H), 1.39–1.27 (m, 8H). $^{13}C$ NMR (75.5 MHZ, $CDCl_3$): δ 194.88, 138.50, 113.90, 33.45, 30.14, 29.28, 28.68 (2 peaks), 28.54, 28.48, 28.18.

Example 11

This example illustrates the preparation of 9-decen-1-thioacetate from 9-decen-1-iodide.

The procedure of Example 9 was followed except that 9-decen-1-iodide was used. The procedure afforded 9-decen-1-thioacetate in 95% yield having the following properties: $^1H$ NMR (300 MHZ, $CDCl_3$): δ 5.88–5.71 (m, 1H), 5.01–4.90 (m, 2H), 2.85 (t, J=7.4 Hz, 2H), 2.32 (s, 3H), 2.03 (m, 2H), 1.53 (m, 2H), 1.39–1.28 (m, IOH). $^{13}C$ NMR (75.5 MHZ, $CDCl_3$): δ 195.91, 139.14, 114.11, 33.76, 30.59, 29.49, 29.45, 29.27, 29.13, 29.03, 28.88, 28.78.

Example 12

This example illustrates the preparation of 10-undecen-1-thioacetate from 10-undecen-1-iodide.

The procedure of Example 9 was followed except that 10-undecen-1-iodide was used. The procedure afforded 10-undecen-1-thioacetate in 95% yield having the following properties: $^1H$ NMR (300 MHZ, $CDCl_3$): δ 5.88–5.71 (m, 1H), 5.02–4.89 (m, 2H), 2.85 (t, J=7.4 Hz, 2H), 2.35 (s, 3H), 2.05 (m, 2H), 1.56 (m, 2H), 1.39–1.28 (m, 12H). $^{13}C$ NMR (75.5 MHZ, $CDCl_3$): δ 195.32, 138.89, 113.98, 33.64, 30.34, 29.40 (2 peaks), 29.27 (2 peaks), 28.95, 28.79 (2 peaks), 28.69.

Example 13

This example illustrates the preparation of 11-dodecen-1-thioacetate from 11-dodecen-1-iodide.

The procedure of Example 9 was followed except that 11-dodecen-1-iodide was used. The procedure afforded 11-dodecen-1-thioacetate in 80% yield having the following properties: $^1H$ NMR (300 MHz, $CDCl_3$): δ 5.88–5.71 (m, 1H), 5.03–4.89 (m, 2H), 2.86 (t, J=7.4 Hz, 2H), 2.33 (s, 3H), 2.03 (m, 2H), 1.55 (m, 2H), 1.38–1.25 (m, 14H). $^{13}C$ NMR (75.5 MHz, $CDCl_3$): δ 195.84, 139.08, 114.03, 33.75, 30.55, 29.39 (3 peaks), 29.07 (3 peaks), 28.87, 28.79 (2 peaks).

RADICAL COUPLING REACTIONS

Example 14

This example illustrates the preparation of 10,10,10-trifluorodecyl thioacetate from the radical coupling of 7-octen-1-thioacetate and 2,2,2-trifluoroethyl iodide after work up and purification.

Step a 0.065 Mole of 7-octen-1-thioacetate and 0.070 mole of 2,2,2-trifluoroethyl iodide were placed in a 50 mL Schlenk flask, and the radical initiator AIBN (2 mole %) was added under a flow of argon. The flask was closed, evacuated until the reaction-mixture started to bubble and filled again with argon; this process was repeated at least 3 times. The flask was left under slight vacuum and the stirred reaction mixture was heated to 90° C. After 3 h, the flask was cooled to room temperature and another portion of AIBN (2 mole %) was added under a flow of argon as described above. The stirred mixture was again heated to 90° C. and the purging process was repeated 2 more times; 3 h passed between each addition of AIBN. The flask was cooled to room temperature, and the crude reaction mixture was transferred to an addition funnel, to which ca. 50 mL of dimethylformamide (DMF) had been added.

Step b 0.2 Mole of $NaBH_4$ was dissolved in 200 ml of DMF (previously degassed) and the mixture cooled to 0° C. The crude product of step (a) was added slowly to the stirred solution. Stirring, at 0° C. under argon was continued for 15 min; the solution was then allowed to warm to room temperature. After stirring for 3 h, 100 mL of ice water was added, and the mixture was stirred until the bubbling ceased. The solution was neutralized with conc. HCl and extracted with hexane. The hexane phases were washed with $H_2O$, dried over $MgSO_4$, and evaporated to dryness.

Step c

The crude reaction mixture from step (b) was mixed with 50 mL of $CH_2Cl_2$. The mixture was cooled to ca. −10° C. (ice/salt bath), and ozone was bubbled through the mixture for 10–20 minutes, depending on the amount of olefinic material in the crude reaction mixture. Completion of the ozonolysis was indicated by bubbling through an aqueous KI solution. The ozonolysis was quenched by bubbling argon through the mixture for 10 minutes. The $CH_2Cl_2$ was gently evaporated at room temperature, and the mixture was transferred to a flask, which had been previously flushed with argon. 100 mL of DMF was added to the flask, and a solution of $NaBH_4$ (2 molar excess) in 50 ml of DMF was added dropwise to the stirred, chilled mixture. After the addition of $NaBH_4$ was complete, the mixture was allowed to warm to room temperature and stirred for 3 h under argon. 100 mL of ice water was then added, the mixture neutralized with conc. HCl and extracted with hexane. The organic phase was washed with $H_2O$, dried over $MgSO_4$ and the solvent was removed by rotary evaporation. The crude product was purified by column chromatography on silica gel (hexane/acetone=1/0, 20/1,10/1) affording 10,10,10-trifluorodecyl thioacetate in 20% yield having the following properties: $^1$H NMR (300 MHz, CDCl$_3$): δ 2.85 (t, J=7.4 Hz, 2H), 2.34 (s, 3H), 2.17–1.99 (m, 2H), 1.58–1.47 (m, 4H), 1.39–1.27 (m, 10H). $^{13}$C NMR (75.5 MHz, CDCl$_3$): δ 195.20, 127.09 (q, $^2J_{CF}$=277 Hz), 33.56 (q, $^2J_{CF}$=27 Hz), 30.52, 29.32, 28.88 (2 peaks), 28.83 (2 peaks), 28.47 (2 peaks), 21.63.

Example 15

This example illustrates the preparation of 11,11,11-trifluoroundecyl thioacetate from the radical coupling of 8-nonen-1-thioacetate and 2,2,2-trifluoroethyl iodide and subsequent work up and purification.

The procedure of Example 14 was followed except that 8-nonen-1-thioacetate was used. The procedure afforded 11,11,11-trifluoroundecyl thioacetate in 20% yield having the following properties: $^1$H NMR (300 MHz, CDCl$_3$): δ 2.86 (t, J=7.4 Hz, 2H), 2.33 (s,3H), 2.17–1.99 (m, 2H), 1.60–1.50 (m, 4H), 1.39–1.25 (m, 12H). $^{13}$C NMR (75.5 MHz, CDCl$_3$): δ 194.95, 127.03 (q, $^2J_{CF}$=276 Hz), 33.72 (q $^2J_{CF}$=28 Hz),30.01, 29.34, 29.13, 29.07, 28.94, 28.84, 28.72, 28.52, 28.45, 21.60.

Example 16

This example illustrates the preparation of 11,11,12,12,13,13,13-heptafluorotridecyl thioacetate from the radical coupling of 8-nonen-1-thioacetate and 1,1,2,2,3,3,3-heptafluoropropyl iodide after work up and purification.

The procedure of Example 14 was followed except that 8-nonen-1-thioacetate and 1,1,2,2,3,3,3-heptafluoropropyl iodide were used. The procedure afforded 11,11,12,12,13,13,13-heptafluorotridecyl thioacetate in 27% yield having the following properties: $^1$H NMR (300 MHz, CDCl$_3$): δ 2.85 (t, J=7.4 Hz, 2H), 2.35 (s, 3H), 2.13–1.93 (m, 214), 1.59–1.49 (m, 4H), 1.39–1.26 (m, 14H). $^{13}$C NMR (75.5 MHz, CDCl$_3$): δ 195.95, 117.91 (tq, $^1J_{CF}$=287 Hz, $^2J_{CF}$=33 Hz), 117.75 (tt, $^1J_{CF}$=252 Hz, $^2J_{CF}$=33 Hz), 108.90 (qtt, $^1J_{CF}$=272 Hz, $^2J_{CF}$=33 Hz) 30.51 (t, $^2J_{CF}$=22 Hz), 29.48, 29.30, 29.26, 29.15 (2 peaks), 29.05 (2 peaks), 28.74, 20.00.

Example 17

This example illustrates the preparation of 12,12,12-trifluorododecyl thioacetate from the radical coupling of 9-decen-1-thioacetate and 2,2,2-trifluoroethyl iodide after work up and purification.

The procedure of Example 14 was followed except that 9-decen-1-thioacetate was used. The procedure afforded 12,12,12-trifluorododecyl thioacetate in 20% yield having the following properties: $^1$H NMR (300 MHz, CDCl$_3$): δ 2.85 (t, J=7.4 Hz, 2H), 2.34 (s, 3H), 2.18–1.99 (m, 2H), 1.61–1.50 (m, 411), 1.39–1.28 (m, 1411). $^{13}$C NMR (75.5 MHz, CDCl$_3$): δ 195.22, 127.06 (q, $^1J_{CF}$=277 Hz), 33.47 (q, $^2J_{CF}$=28 Hz), 30.17, 29.36, 29.24 (2 peaks), 29.14, 28.98, 28.90, 28.83, 28.60, 28.50, 21.64.

Example 18

This example illustrates the preparation of 12,12,13,13,13-pentafluorotridecyl thioacetate from the radical coupling of 9-decen-1-thioacetate and 1,1,2,2,2-pentafluoroethyl iodide after work up and purification.

The procedure of Example 14 was followed except that 9-decen-1-thioacetate and 11,2,2,2-pentafluoroethyl iodide were used. The procedure afforded 12,12,13,13,13-pentafluorotridecyl thioacetate in 29% yield having the following properties: $^1$H NMR (300 MHz, CDCl$_3$): δ 2.85 (t, J=7.4 Hz, 2H), 2.35 (s, 3H), 2.12–1.91 (m, 2H), 1.59–1.50 (m, 4H), 1.39–1.26 (m, 14H). $^{13}$C NMR (75.5 MHz, CDCl$_3$): a 195.38, 118.73 (tq, $^1J_{CF}$=284 Hz, $^2J_{CF}$=37 Hz), 115.73 (qt, $^1J_{CF}$=251 Hz, $^2J_{CF}$=37 Hz), 30.51 (t, $^2J_{CF}$=20 Hz), 29.41 (2 peaks), 29.29 (2 peaks), 29.19, 29.04, 28.94 (3 peaks), 28.65, 20.09.

Example 19

This example illustrates the preparation of 12.12,13,13,14,14,14-heptafluorotetradecyl thioacetate from the radical coupling of 9-decen-1-thioacetate and 1,1,2,2,3,3,3-heptafluoropropyl iodide after work up and purification.

The procedure of Example 14 was followed except that 9-decen-1-thioacetate and 1,1,2,2,3,3,3-heptafluoropropyl iodide were used. The procedure afforded 12,12,13,13,14,14,14-heptafluorotetradecyl thioacetate in 20% yield having the following properties: $^1$H NMR (300 MHz, CDCl$_3$): δ 2.85 (t, J=7.4 Hz, 2H), 2.35 (s, 3H), 2.13–1.93 (m, 2H), 1.59–1.49 (m, 4H), 1.39–1.26 (m, 14H). $^{13}$C NMR (75.5 MHz, CDCl$_3$): δ 195.45, 117.76 (tq, $^1J_{CF}$=272 Hz, q, $^2J_{CF}$=33 Hz), 117.59 (tt, $^1J_{CF}$=260 Hz, q, $^2J_{CF}$=33 Hz), 108.86 (qtt, $^1J_{CF}$=272 Hz, q, $^2J_{CF}$=33 Hz), 30.43 (t, $^2J_{CF}$=33 Hz), 29.42, 29.28 (2 peaks), 29.20, 29.06, 28.93 (3 peaks), 28.87, 28.64, 19.92.

Example 20

This example illustrates the preparation of 13,13,13-trifluorotridecyl thioacetate from the radical coupling of 10-undecen-1-thioacetate and 2,2,2-trifluoroethyl iodide after work up and purification.

The procedure of Example 14 was followed except that 10-undecen-1-thioacetate was used. The procedure afforded 13,13,13-trifluorotridecyl thioacetate in 20% yield having the following properties: $^1$H NMR (300 MHz, CDCl$_3$): δ 2.85 (t, J=7.4 Hz, 2H). 2.35 (s, 3H), 2.16–1.98 (m, 2H), 1.59–1.49 (m, 4H), 1.39–1.26 (m, 16H). $^{13}$C NMR (75.5 MHz, CDCl$_3$): δ 195.51, 127.15 (q, $^1J_{CF}$=276 Hz), 33.56 (q, $^2J_{CF}$=27 Hz), 30.33, 29.37 (3 peaks), 29.24, 29.06, 28.98 (2 peaks), 28.68 (2 peaks) 28.59, 21.71.

Example 21

This example illustrates the preparation of 13,13,14,14,14-pentafluorotetradecyl thioacetate from the radical coupling of 10-undecen-1-thioacetate and 1,1,2,2,2-pentafluoroethyl iodide after work up and purification.

The procedure of Example 14 was followed except that 10-undecen-1-thioacetate and 1,1,2,2,2-pentafluoroethyl iodide were used. The procedure afforded 13,13,14,14,14-pentafluorotridecyl thioacetate in 20% yield having the following properties: $^1$H NMR (300 MHz, CDCl$_3$): δ 2.86 (t, J=7.4 Hz, 211), 2.35 (s, 3H), 2.11–1.91 (m, 2H), 1.59–1.49 (m, 4H), 1.39–1.25 (m, 16H). $^{13}$C NMR (75.5 MHz, CDCl$_3$): δ 195.39, 119.13 (tq, $^1J_{CF}$=284 Hz, $^2J_{CF}$=37 Hz), 115.70 (qt, $^1J_{CF}$=251 Hz, $^2J_{CF}$=37 Hz), 30.49 (t, $^2J_{CF}$=20 Hz), 29.36 (3 peaks), 29.21 (2 peaks). 29.04(2 peaks). 28.93 (3 peaks), 28.66, 20.08.

Example 22

This example illustrates the preparation of 14,14,14-trifluorotetradecyl thioacetate from the radical coupling of 11-dodecen-1-thioacetate and 2,2,2-trifluoroethyl iodide and subsequent work up and purification.

The procedure of Example 14 was followed except that 11-dodecen-1-thioacetate was used. The procedure afforded 14,14,14-trifluorotetradecyl thioacetate in 20% yield having the following properties: $^1$H NMR (300 MHz, CDCl$_3$): δ

2.87 (t, J=7.4 Hz, 2H), 2.36 (s, 3H), 2.16–1.97 (m, 2H), 1.60–1.49 (m, 4H), 1.38–1.23 (m, 18H). $^{13}$C NMR (75.5 MHz, CDCl$_3$): δ 195.85, 127.23 (q, $^1J_{CF}$=276 Hz), 33.66 (q, $^2J_{CF}$=27 Hz), 30.50, 29.47 (4 peaks), 29.41, 29.30, 29.13, 29.06 (2 peaks), 28.76, 28.65, 21.79.

DEBLOCKING REACTIONS

Example 23

This example illustrates the preparation of 10,10,10-trifluorodecanethiol from 10,10,10-trifluorodecyl thioacetate after work up and purification.

0.015 Mole of 10,10,10-trifluorodecyl thioacetate in 100 mL of absolute ethanol (degassed by bubbling with argon) were placed in a 250 mL flask under argon. To the solution, 40 mL of conc. HCl were added, and the stirred mixture was heated under reflux at 90° C. for 13 h. The reaction mixture was concentrated in vacuo, and the resultant oil was suspended in 30 mL of 1H$_2$O. The mixture was extracted with ether, and the ether layers were washed with H$_2$O, dried over MgSO$_4$, and evaporated to dryness. The crude product was purified by column chromatography on silica gel (hexane/acetone=1/0, 40/1) to obtain 10,10,10-trifluorodecanethiol which usually contained ca. 10% of the corresponding disulfide. The overall yield was about 90%. 10,10,10-trifluorodecanethiol had the following properties: $^1$H NMR (300 MHz, CDCl$_3$): δ 2.52 (dt, J=7.2 Hz, 2H), 2.13–1.96 (m, 2H), 1.67–1.53 (m, 2H) 1.59–1.47 (m, 2H), 1.36–1.25 (m, 11H). $^{13}$C NMR (75.5 MHz, CDCl$_3$): δ 127.25 (q, $^1J_{CF}$=276 Hz), 34.03, 33.50 (q, $^2J_{CF}$=28 Hz), 29.11 (3 peaks), 28.95, 28.25, 24.61, 21.81. Bis-(10,10,10-trifluorodecyl) disulfide had the following properties: $^1$H NMR (300 MHz, CDCl$_3$): δ 2.67 (t, J=7.4 Hz, 4H), 2.13–1.96 (m, 4H), 1.67–1.53 (m, 4H), 1.59–1.47 (m, 4H), 1.36–1.25 (m, 20H).

Example 24

This example illustrates the preparation of from 11,11,11-trifluoroundecanethiol from the 11,11,11-trifluoroundecyl thioacetate after work up and purification.

The procedure of Example 24 was followed except that 11,11,11-trifluoroundecyl thioacetate was used. The procedure afforded 11,11,11-trifluoroundecanethiol and the disulfide (ca. 10%) in about a 90% yield. 11,11,11-trifluoroundecanethiol had the following properties: $^1$H NMR (300 MHz, CDCl$_3$): δ 2.52 (dt, J=7.2 Hz, 2H), 2.13–1.95 (m, 2H), 1.67–1.53 (m, 2H), 1.58–1.48 (m, 2H), 1.36–1.25 (m, 13H). $^{13}$C NMR (75.5 MHz, CDCl$_3$): δ 127.18 (q, $^1J_{CF}$=276 Hz), 34.02,33.50 (q, $^2J_{CF}$=28 Hz), 29.36, 29.25, 29.13 (2 peaks), 28.63, 28.30, 24.48, 21.78. Bis-(11,11,11-trifluoroundecyl) disulfide had the following properties: $^1$H NMR (300 MHz, CDCl$_3$): δ 2.67 (t, J=7.4 Hz, 4H), 2.13–1.95 (m, 4H), 1.67–1.53 (m, 4H), 1.58–1.48 (m, 4H), 1.36–1.25 (m, 24H).

Example 25

This example illustrates the preparation of 11,11,12,12,13,13,13-heptafluorotridecanethiol from 11,11,12,12,13,13,13-heptafluorotridecyl thioacetate after work up and purification.

The procedure of Example 24 was followed except that 11,11,12,12,13,13,13-heptafluorotridecyl thioacetate was used. The procedure afforded 11,11,12,12,13,13,13-heptafluorotridecanethiol in 90% yield (ca. 10% disulfide). 11,11,12,12,13,13,13-heptalluorotridecanethiol had the following properties: $^1$H NMR (300 MHz, CDCl$_3$): δ 2.51 (dt, J=7.2 Hz, 2H), 2.11–1.93 (m, 2H), 1.66–1.53 (m, 2H), 1.40–1.22 (m, 15H). $^{13}$C NMR (75.5 MHz, CDCl$_3$): δ 117.87 (tq, $^1J_{CF}$=287 Hz, $^2J_{CF}$=34 Hz), 117.72 (tt, $^1J_{CF}$=252 Hz, $^2J_{CF}$=31 Hz), 108.86 (qtt, $^1J_{CF}$=267 Hz, $^1J_{CF}$=37 Hz), 33.97, 30.54 (t, $^2J_{CF}$=22 Hz), 29.34, 29.24, 29.13 (2 peaks), 29.02, 28.29, 24.57, 19.98. Bis-(11,11,12,12,13,13,13-heptafluorotridecyl) disulfide had the following properties: $^1$H NMR (300 MHz, CDCl$_3$): δ 2.68 (t, J=7.4 Hz, 4H), 2.17–1.94 (m, 4H), 1.66–1.53 (m, 4H), 1.60–1.44 (m, 4H), 1.37–1.21 (m, 28H).

Example 26

This example illustrates the preparation of 12,12,12-trifluorododecanethiol from 12,12,12-trifluorododecyl thioacetate after work up and purification.

The procedure of Example 24 was followed except that 12,12,12-trifluorododecyl thioacetate was used. The procedure afforded 12,12,12-trifluorododecanethiol in about a 90% yield (ca. 10% disulfide). 12,12,12-trifluorododecanethiol had the following properties: $^1$H NMR (300 MHz, CDCl$_3$): δ 2.52 (dt, J=7.2 Hz, 2H), 2.13–1.96 (m, 2H), 1.67–1.53 (m,2H), 1.59–1.47 (m, 2H), 1.36–1.25 (m, 15H). $^{13}$C NMR (75.5 MHz, CDCl$_3$): δ 127.25 (q, $^1J_{CF}$=277 Hz), 33.98,33.60 (q, $^2J_{CF}$=28 Hz), 29.39 (2 peaks), 29.26, 29.10, 28.98, 28.60, 28.28, 24.48, 21.75. Bis-(12,12,12-trifluorododecyl) disulfide had the following properties: $^1$H NMR (300 MHz, CDCl$_3$): δ 2.67 (t, J=7.4 Hz, 4H), 2.13–1.95 (m, 4H), 1.67–1.53 (m, 4H), 1.58–1.48 (m, 4H), 1.36–1.25 (m, 28H).

Example 27

This example illustrates the preparation of 12,12,13,13,13-pentafluorotridecanethiol from 12,12,13,13,13-pentafluorotridecyl thioacetate after work up and purification.

The procedure of Example 24 was followed except that 12,12,13,13,13-pentafluorotridecyl thioacetate was used. The procedure afforded 12,12,13,13,13-pentafluorotridecanethiol in 91% yield (ca. 10% disulfide). 12,12,13,13,13-pentafluorotridecanethiol had the following properties: $^1$H NMR (300 MHz, CDCl$_3$): δ 2.52 (t, J=7.2 Hz, 2H), 2.08–1.92 (m, 2H), 1.63–1.52 (m, 2H), 1.58–1.41 (m, 2H), 1.35–1.23 (m, 15H). $^{13}$C NMR (75.5 MHz, CDCl$_3$): δ 119.02 (tq, $^1J_{CF}$=249 HZ, $^2J_{CF}$=37 Hz), 115.79 (qt, $^1J_{CF}$=249 Hz, $^2J_{CF}$=37 Hz), 34.09, 30.62 (t, $^2J_{CF}$=22 Hz), 29.46 (2 peaks), 29.34, 29.18, 29.07 (2 peaks), 28.35, 24.47, 20.19. Bis-(12,12,13,13,13-pentafluorotridecyl) disulfide had the following properties: $^1$H NMR (300 MHz, CDCl$_3$): δ 2.67 (t, J=7.4 Hz, 4H), 2.08–1.92 (m, 4H), 1.63–1.52 (m, 4H), 1.58–1.41 (m, 4H), 1.35–1.23 (m, 28H).

Example 28

This example illustrates the preparation of 12,12,13,13,14,14,14-heptafluorotetradecanethiol from 12,12,13,13,14,14,14-heptafluorotetradecyl thioacetate after work up and purification.

The procedure of Example 24 was followed except that 12,12,13,13,14,14,14-heptafluorotetradecyl thioacetate was used. The procedure afforded 12,12,13,13,14,14,14-heptafluorotetradecanethiol in 94% yield (ca. 10% disulfide). 12,12,13,13,14,14,14-heptafluorotetradecanethiol had the following properties: $^1$H NMR (300 MHz, CDCl$_3$): δ 2.52 (dt, J=7.2 Hz, 2H), 2.17–1.94 (m, 2H), 1.66–1.53 (m, 2H), 1.60–1.44 (m, 2H), 1.37–1.21 (m, 15H). $^{13}$C NMR (75.5 MHz, CDCl$_3$): δ 117.86 (tq, $^1J^{CF}$=287 Hz, q, $^2J_{CF}$=37

Hz), 117.67 (tt, $^1J_{CF}$=252 Hz, q, $^2J_{CF}$=31 Hz), 108.85 (qtt, $^1J_{CF}$=263 Hz, q, $^2J_{CF}$=37 Hz), 34.01, 30.47 (t, $^2J_{CF}$=22 Hz), 29.39 (2 peaks), 29.28, 29.13, 28.99 (2 peaks), 28.28, 24.42, 19.93. Bis-(12,12.13.13.14,14,14-heptafluorotetradecyl) disulfide had the following properties: $^1$H NMR (300 MHz, CDCl$_3$): δ 2.68 (t, J=7.4 Hz, 4H), 2.17–1.94 (m, 4H), 1.66–1.53 (m, 4H), 1.60–1.44 (m, 4H), 1.37–1.21 (m, 28H).

Example 29

This example illustrates the preparation of 13,13,13-trifluorotridecanethiol from 13,13,13-trifluorotridecyl thioacetate after work up and purification.

The procedure of Example 24 was followed except that 13,13,13-trifluorotridecyl thioacetate was used. The procedure afforded 13,13,13-trifluorotridecanethiol in 86% yield (ca. 10% disulfide). 13,13,13-trifluorotridecanethiol had the following properties: $^1$H NMR (300 MHz, CDCl$_3$): δ 2.52 (dt, J=7.2 Hz, 2H), 2.11–1.96 (m, 2H), 1.62–1.51 (m, 2H), 1.57–1.47 (m, 211), 1.35–1.23 (m, 17H). $^{13}$C NMR (75.5 MHz. CDCl$_3$): 67 127.11 (q, $^1J_{CF}$=276 Hz), 34.00, 33.55 (q, $^2J_{CF}$=28 Hz), 29.42 (3 peaks), 29.26, 29.07, 28.98, 28.58, 28.25, 24.31, 21.71. Anal. Calc'd for C$_{13}$H$_{25}$F$_3$S: C, 57.75; H, 9.32. Found: C, 57.45; H, 9.34. Bis-(13,13,13-trifluorotridecyl) disulfide had the following properties: $^1$H NMR (300 MHz, CDCl$_3$): δ 2.63 (dt, J=7.4 Hz, 4H), 2.11–1.96 (m, 4H), 1.62–1.51 (m, 4H), 1.57–1.47 (m, 411), 1.35–1.23 (m, 3211).

Example 30

This example illustrates the preparation of 13,13,14,14,14-pentafluorotetradecanethiol from 13,13,14,14,14-pentafluorotetradecyl thioacetate after work up and purification.

The procedure of Example 24 was followed except that 13,13,14,14,14-pentafluorotetradecyl thioacetate was used. The procedure afforded 13,13,14,14,14-pentafluorotetradecanethiol in 93% yield (ca. 10% disulfide). 13,13,14,14,14-pentafluorotetradecanethiol had the following properties: $^1$H NMR (300 MHz, CDCl$_3$): δ 2.52 (dt, J=7.2 Hz, 2H), 2.08–1.92 (m, 2H), 1.63–1.52 (m, 2H), 1.58–1.41 (m, 2H), 1.35–1.23 (m, 17H). $^{13}$C NMR (75.5 MHz, CDCl$_3$): δ 119.09 (tq, $^1J_{CF}$=285 Hz, $^2J_{CF}$=37 Hz), 115.62 (qt, $^1J_{CF}$=252 Hz, $^2J_{CF}$=37 Hz), 33.95, 30.41 (t, $^2J_{CF}$=22 Hz), 29.37 (3 peaks), 29.22, 29.04, 28.91 (2 peaks), 28.20, 24.29, 20.03. Bis-(13,13,14,14,14-pentafluorotetradecyl) disulfidehad the following properties: $^1$H NMR (300 MHz, CDCl$_3$): δ 2.67 (t, J=7.4 Hz, 4H), 2.08–1.92 (m, 4H), 1.63–1.52 (m, 4H), 1.58–1.41 (m, 4H), 1.35–1.23 (m, 32H).

Example 31

This example illustrates the preparation of 14,14,14-trifluorotetradecanethiol from 14,14,14-trifluorotetradecyl thioacetate after work up and purification.

The procedure of Example 24 was followed except that 14,14,14-trifluorotetradecyl thioacetate was used. The procedure afforded 14,14,14-trifluorotetradecyanethiol in % yield (ca. 10% disulfide). 14,14,14-trifluorotetradecyanethiol had the following properties: $^1$H NMR (300 MHz, CDCl$_3$): δ 2.48 (dt, J=7.2 Hz, 2H), 2.11–1.95 (m, 2H), 1.62–1.50 (m, 2H), 1.58–1.46 (m, 2H), 1.34–1.23 (m, 191H). $^{13}$C NMR (75.5 MHz, CDCl$_3$): δ 127.15 (q, $^1J_{CF}$=276 Hz), 34.03, 33.46 (q, $^2J_{CF}$=29 Hz), 29.50 (4 peaks), 29.31, 29.13, 29.03, 28.65, 28.32, 24.49, 21.77. Anal. Calc'd for C$_{14}$H$_{27}$F$_3$S: C, 59.12; H, 9.57.

Found: C, 59.50; H, 9.90. Bis-(14,14,14-trifluorotetradecyl) disulfide had the following properties: $^1$H NMR (300 MHz, CDCl$_3$): δ 2.62 (t, J=7.4 Hz, 4H), 2.11–1.95 (m, 4H), 1.62–1.50 (m, 4H), 1.58–1.46 (m, 4H), 1.34–1.23 (m, 36H).

AROMATIC SURFACE MODIFYING AGENTS

Example 32

This example illustrates the synthesis of 1,2-bis(mercaptomethyl)-4,5-dipentylbenzene was synthesized following Schemes 1, 11 and III using the synthetic schemes set forth in FIG. 5.

Reagents and Equipment

Ether, THF and toluene were purchased from EM Sciences and dried by passing through alumina column, and degassed by freeze-pump-thaw methods before use. Phthalaldehyde, camphorsulfonic acid, palladium on 10% activated carbon, paraformaldehyde, p-toluenesulfonic acid monohydrate and 1,2-dichlorobenzene were purchased from Aldrich. Hydrobromic acid 33 wt % in acetic acid (Janssen Chimicaor, Acros) and acetic acid (EM Science) were used without modification. Nuclear Magnetic Resonance spectra were recorded on a General Electric QE-300 MHz spectrometer at 300 MHz for $^1$H and 75 MHz for $^{13}$C. The NMR spectra were taken in CDCl$_3$ and referenced to 7.24 for $^1$H NMR and 77.000 for $^{13}$C NMR. Column chromatography was carried out on silica gel (60–200 mesh) from EM Sciences. Thin layer chromatograhy (TLC) was carried out on 250 mm thick Whatman silica gel plates. The spots were detected under UV lamp or in an iodine chamber.

Synthesis of 1,2-di(n-pentyl)benzene (5c) Using Scheme I of FIG. 5

Synthesis of 1,2-di(1'-hydroxypentyl)benzene (a)

This intermediate was synthesized by addition of n-BuLi to phthalaldehyde. A 200 mL Schlenk flask equipped with a magnetic stir bar was attached to a 60 mL dropping funnel with other end capped with a rubber septum. This apparatus was then flame dried twice under argon. A separate 250 mL oven dried round bottom flask was charged with 1 g (8.1 mmol) phthalaldehyde, capped with a rubber septum, and purged with argon for 15 min. Dry and degassed ether (60 mL) was then added via cannula. This solution of phthalaldehyde in diethyl ether was transferred via cannula to the Schlenk flask. The flask was cooled to 0° C. in an ice bath, and 10.0 mL (24.2 mmol) of a 2.0 M solution of n-BuLi in diethyl ether was added dropwise via dropping funnel. The solution was stirred for 6 h and allowed to warm slowly to room temperature. The ether layer was washed with dilute HCl (3×50 mL), brine (1×50 mL), dried over MgSO$_4$, and concentrated by rotary evaporation to give 1.6 g (6.4 mmol, 79% yield) of 5a: $^1$H NMR (300 MHz, CDCl3): δ 0.88 (6H, t, J=8 Hz, CH$_3$), 1.25–1.5 (12H, m), 4.97(2H, t, J=5.7 Hz, CHOH), 7.27(2H, d of "d", $J_{1,2}$=7.5 Hz, $J_{1,3}$=2.8 Hz, Ar—H), 7.43(2H, d of "d", $J_{1,2}$=7.5 Hz, $J_{1,3}$=2.8 Hz, Ar—H). The product of the reaction was usually a mixture of 51 and 5b, which was dehydrated in the next step without further purification.

Synthesis of 1,2-di(pent-1'-enyl)benzene (5b)

A 500 mL round-bottomed flask with a magnetic stir bar was charged with 1.0 g (4.5 mmol) of camphorsulfonic acid and 400 mL of benzene. The flask was placed in a 60° C. oil bath, and stirring was initiated. Camphorsulfonic acid was dissolved in benzene, and 5.59 g of 5a (22 mmol) was slowly added with a pipet. After the addition was complete, a double walled reflux condenser was attached to the round-bottomed flask and a drying tube packed with dririte was fitted to the other side of the condenser. The mixture was refluxed for 4–5 h, and small portions of benzene were distilled off in 1 h intervals of refluxing, until little starting material remained by analysis by TLC in hexanes. Hexanes (50 mL) were added to the reaction mixture and the solution was washed with saturated $NaHCO_3$ (3×50 mL), brine (1×50 mL), dried over $MgSO_4$, and concentrated under vacuum. The residual oil was chromatographed using hexanes and gave 1.25 g (5.84 mmol, 26% yield) of a mixture of cis and trans isomers of 1,2-di(pent-1'-enyl) benzene as a pale yellow oil: $^1$H NMR (300 MHz, $CDCl_3$): δ 0.88 (6H, t, J=8 Hz, $CH_3$), 1.25–1.5(12H, m), 2.21 (2H, m, $CH_2CH=CH$), 6.04 (2H, t of "d", $J_{ab}$=15.6 Hz, $J_{ax}$=6.9 Hz, $CH_2CH=CH$), 6.55 (2H, d, $J_{ab}$=15.6 Hz, CH=CHAr), 7.27(2H, d of "d", $J_{1,2}$=7.5 Hz, $J_{1,3}$=3.6 Hz, Ar—H, 7.43 (2H, d of "d",$J_{1,2}$=7.5 Hz, $J_{1,3}$=3.6 Hz, Ar—H). $^{13}$C NMR (75 MHz, $CDCl_3$): δ 13.68, 13.70, 14.1, 29.4, 29.71, 29.75, 31.9, 35.5, 35.42, 35.48, 126.26, 126.32, 126.35, 126.39, 126.8, 128.0, 128.1, 132.8, 132.9, 135.8. The reported spectral data is for the mixture of cis and trans isomers of 5b. The alkene derivative 5b obtained after reaction was hydrogenated in the next step without separating the cis and trans isomers.

Synthesis of 1,2-di-(n-pentyl)benzene (5c)

An oven dried 250 mL round-bottom ed flask equipped with a magnetic stir bar was charged with catalytic amount (~100 mg) of 10% palladium on carbon, capped with a rubber septum, and purged with argon for 15 min. A separate 250 mL round bottom flask containing 200 mL of hexanes was capped with a rubber septum and the solvent was bubbled with argon for 25–30 min. Hexanes (40 mL) was added via cannula to the flask containing palladium and the suspension was stirred under hydrogen for 25–30 min. Separately, a 250 mL round-bottomed flask was charged with 1.25 g (5.84 mmol) of 5b, capped the flask with rubber septum and purged with argon for 15 min. Hexanes (40 mL) was transferred via cannula to the flask containing 5b and was bubbled with hydrogen for 20–25 min. The solution was added via cannula to the palladium suspension in hexanes. The solution was stirred under hydrogen for 4 h at rt after which no olefinic peaks of starting material were observed by NMR. The solution was filtered through a small silica gel column using hexanes. The filtrate was then concentrated by rotary evaporation to give 1.27 g (5.83 mmol, 100% yield) of 5c as a colorless liquid: $^1$H NMR (300 MHz $CDCl_3$): δ 0.90 (6H, t, J=7 Hz, $CH_3$), 1.36–1.57 (12H, m), 2.59 (4H, t, J=8 Hz $CH_2$ Ar), 7.08–7.15(4H, m, Ar—H). $^{13}$C NMR (75 MHz, $CDCl_3$): δ 14.0, 22.6, 31.1, 32.0, 32.7, 125.7, 129.1, 140.5.

Synthesis of 1,2-di(n-pentyl)benzene (5c) Using Scheme II of FIG. 5

Another method used to synthesize 5c was by grignards coupling reaction of 1,2-dichlorobenzene with n-pentylmagnesium bromide (scheme II). A 200 mL Schlenk flask equipped with a magnetic stir bar was attached to a 60 mL dropping funnel. The funnel was capped with a rubber septum, and the entire apparatus was flame-dried under argon. A separate 250 mL oven-dried round-bottomed flask was charged with 8.6 mL (7.7 mmol) 1,2-dichlorobenzene and a catalytic amount (~0.1 g) of dichloro [1,3-bis (diphenylphosphine) propane] nickel(II). The flask was capped with a rubber septum and purged with argon for 15 min. Dry and degassed diethyl ether (60 mL) was subsequently added, and the solution was transferred via cannula to the Schlenk flask. The flask was placed in a ice bath at 0° C., and a 75 mL (0.19 mol) portion of a 2.6 M solution of n-pentylmagnesium bromide in diethyl ether was added dropwise via dropping funnel. After the addition was complete the solution was warmed to rt and refluxed for 12 h. A 2 N solution of HCl was carefully added via pipet to destroy any excess Grignard reagent. The addition was stopped when a aqueous layer was obtained. The aqueous layer was separated and extracted with a mixture of hexanes/$Et_2O$ (3×50 mL). The organic extracts were combined and washed with $H_2O$ (1×50 mL), saturated $Na_2CO_3$ (1×50 mL) and $H_2O$ (1×50 mL). The solution was dried over $MgSO_4$, and concentrated by rotary evaporation. The residual oil was chromatographed on silica gel by using hexanes to yield 15 g (76.9 mmol, 90% yield) of 5c as a colorless liquid.

1,2-Bis(mercaptomethyl)4,5-dipentylbenzene (5f) Using Scheme III of FIG. 5

Synthesis of 1,2-Bis(bromomethyl)-4,5-dipentylbenzene (5d)

A 100 mL cylindrical high pressure glass vessel equipped with a magnetic stirring bar was charged with 0.50 g (2.3) mmol) of 5c, 10 mL of acetic acid, 0.25 g (8.3 mmol) of paraformaldehyde and 1 mL of 33 wt % hydrobromic acid in acetic acid. The resulting mixture was heated with stirring at 110° C. for 6 days. Hydrobromic acid solution (~1 mL) and paraformaldehyde (~0.25 g) were added twice during the course of the reaction. Aliquots of the reaction mixture were removed via pipet, and analyzed by $^1$H NMR spectroscopy. Formation of the mono-bromomethylated (δ 4.48, 2H, s, $ArCH_2$ Br) was initially observed. The peak corresponding to the bis-bromomethylated 5d (δ 4.65, 4H, s, $ArCH_2Br$) increased while that of mono-bromomethylated decreased. Water (10 mL) was added, and the mixture was transferred to a 500 mL separatory funnel using hexanes and $Et_2O$. The organic phase was washed with sat'd $NaHCO_3$ (3×50 mL) and sat'd brine (1×50 mL), and dried ($MgSO_4$). Removal of the solvent by rotary evaporation gave an oil that was chromatographed on silica gel using hexanes to yield 0.49 g (1.2 mmol, 45%) of a pale yellow oil, which consisted of a mixture of mono- and bis-bromomethylated products in a 3:7 ratio, respectively. The products were cleanly separated by reversed-phase chromatography on a Water μBondpack $C_{18}$ column (7.8×300 mm) using a mixture of $THF/H_2O$ (60/40) at a flow rate of 4 mL/min. Mixtures derived from the other substrates could also be efficiently separated. Analytical data for mono-bromomethylated product: $^1$H NMR (300 MHz, CDC $1_3$): δ 0.89 (t, 6H, J=8 Hz, $CH_3$), 1.25–1.50 (m, 12H), 2.54 (t, 4H, J=8 Hz, $CH_2Ar$), 4.48 (s, 2H, $CH_2Br$), 7.10–7.15 (m, 3H, Ar—H). GC/MS data: m/z (rel. intensity; ion), 310,312 (5%,5%; $M^+$),231 (100%,$M^+$—Br). HRMS calcd for $C_{17}H_{27}{}^{81}Br(M^+)$:312.1278. Found:312.1277. Analytical data for 5d: $^1$H NMR (300 MHz, $CDCl_3$): δ 0.89 (t, 6H, J=8 Hz, $CH_3$), 1.25–1.50 (m, 12H), 2.54 (t, 4H, J=8 Hz, $CH_2Ar$), 4.65 (s, 4H, $CH_2Br$), 7.11 (s, 2H, Ar—H). $^{13}$C NMR (75 MHz, $CDCl_3$): δ 14.0, 22.5, 30.6, 30.7, 31.9, 32.3, 131.8, 131.9, 133.6, 142.3. GC/MS (70 eV, EI): m/z (rel. intensity; ion) 402, 404, 406 (1.2%, 2.5%, 1.1%; $M^+$), 323, 325 (100%, 99%; $M^+$—Br), 244 (31%: $M^+$—2Br), 91 (12%; $C_7H_7{}^+$). HRMS calculated for $C_{18}H_{28}{}^{81}Br_2(M^+)$: 406.0521. Found: 406.0525.

Synthesis of 1,2-Bis(thioacetyl)-4,5-dipentylbenzene (5e)

A 100 mL round-bottomed flask equipped with a magnetic stir bar charged with 0.50 g (4.1 mmol) of potassium thioacetate and 15 mL of absolute ethanol. After the potassium thioacetate dissolved in the ethanol, a mixture of monobromomethylated intermediate 5d (0.41 g; ca. 0.7 mmol of 5d) was dissolved in 15 mL of hexanes and slowly added via pipet. The resulting mixture was refluxed for 6 h under a slow flow of argon. The reaction mixture was cooled, and evaporated to dryness by rotary evaporation. Water (20 mL) was added to the obtained residue and the suspension was extracted with a mixtures of hexanes/Et$_2$O (3×50 mL), dried over MgSO$_4$ and concentrated by rotary evaporation. The residual oil was chromatographed using hexanes to give 0.10 g (0.25 mmol, ca. 40% yield) of 5e as a colorless liquid: $^1$H NMR (300 MHz, CDCl$_3$): δ 0.88 (6H, t, J=8 Hz, CH$_3$), 1.32–1.52 (12H, m), 2.32(6H, s, COCH$_3$), 2.49(4H, t, J=8 Hz, CH$_2$Ar), 4.10 (4H, s, SCH$_2$), 7.03(2H, m, Ar—H). $^{13}$C NMR (75 MHz, CDCl$_3$): δ 14.0, 22.5, 30.3, 30.7, 30.8, 31.9, 32.2, 131.3, 132.5, 140.5, 195.0.

Synthesis of 1,2-bis(mercaptomethyl)-4,5-dipentylbenzene (5f)

A 250 mL two necked round bottom flask equipped with a magnetic stir bar and a reflux condenser was charged with 0.28 g (7.5 mmol) of lithium aluminum hydride (LAH) and 10 mL of dry THF. The apparatus was purged with argon and a solution of 5e (0.98 g; 2.5 mmol) in dry THF was transferred via cannula to the LAH suspension under argon. The mixture was refluxed under argon for 2 h. After cooling the flask to rt, ice cold water was added dropwise carefully. Upon observation of a white precipitate, conc. HCl was rapidly added, followed by more cold water. The aqueous layer was extracted with a mixture of hexanes/Et$_2$0 (3×50 mL). The organic extracts were combined together, washed with saturated NaHCO$_3$ (2×50 mL), brine (1×50 mL), dried over MgSO$_4$ and concentrated by rotary evaporation. The residual oil was chromatographed on silica gel using a mixture of hexanes/Et$_2$O (60/1) and gave 0.61 g (2.0 mmol, 80% yield) of 5f as a colorless liquid. $^1$H NMR (300 MHz, CDCl$_3$): δ 0.91 (6H, t, J=7 Hz, CH$_3$), 1.36–1.57 (12H, m), 1.85 (1H, t, SH), 2.53 (4H, t, J=8 Hz, CH$_2$Ar), 3.79 (4H, d, SCH$_2$), 7.04 (2H, s, Ar—H). $^{13}$C NMR (75 MHz, CDCl$_3$): δ 14.0, 22.5, 25.8, 30.9, 31.9, 32.2, 130.32, 130.38, 135.7 and 140.3.

CIS/TRANS TETRA SUBSTITUTED ETHENE SURFACE MODIFYING AGENTS

Example 33

This example illustrates the general synthetic procedure for synthesizing cis or trans tetra substituted surface modifying agents and the preparation of trans-2,3-ditetradecyl-2-butene-1,4-dithiol is demonstrated using the synthetic scheme set forth in FIG. 6.

General Procedures $^1$H NMR (300 MHz) and $^{13}$C NMR (75 MHz) were obtained on a GE-300 (300 MHz) spectrometer with CDCl$_3$ as a solvent. All experiments were performed under an argon atmosphere and reagent grade tetrahydrofuran was dried by passage through activated alumina and degassed by using the Freeze-Pump-thaw methods. HMPA was dried over calcium hydride and then transferred to the flask containing Na under argon. Distillation of HMPA was performned after 24 h to give pure and dried HMPA. Triethyl phosphite was dried over calcium hydride and then distilled before use. Cuprous bromide-dimethyl sulfide was purchased from Aldrich and recylstallized before use because reaction yields depend on the purity of this reagent. Alkyl iodides were purchased or synthesized by previously known methods and then purified by chromathography on silica gel before use. Al organocopper complexes (1.1 equiv. of DMAD) were prepared from a stoichiometric amount of copper complexes and Grignard reagents in THF (10 mL) at −50° for 1 h. All conjugate-addition reactions were performed at −78° C.

Synthesis of dimethyl trans-2,3-ditetradecylbutenedioate.

Tetradecylmagnesium chloride (11 mmol) in tetradyrofuran was added to a suspension of copper bromide dimethyl sulfide (11 mmol) in tetradyrofuran at −50° C. and the reaction mixture was stirred for 1 h. Dimethyl acetylene dicarboxylate (10 mmol) in tetradydrofuran was added at −78° C. and the reaction mixture was stirred for 1 h at −78° C. To a solution of organic vinyl cuprate at −78° C. was successively added hexamethylphosphoric triamide (20 mmol), dodecyl iodide (20 mmol), and finally triethyl phosphite (30 mmol). The mixture was slowly allowed to reach (over 3 h) room temperature, stirred overnight at room temperature then quenched with sat'd NH$_4$Cl solution at −30° C. The aqueous layer was extracted with diethyl ether. The combined organic layers were washed with sat'd NaCl solution and sat'd NH$_4$ Cl solution and dried with anhydrous magnesium sulfate. Solvents were evaporated under vacuum and the products were isolated by silica gel column chromatography (hexane/ethyl acetate=99.5/0.5). The reaction affored dimethyl trans-2,3-ditetradecylbutenedioate in 78% yield $^1$H NMR (300 MHz, CDCl$_3$): δ 3.77 (s, 6H, CO$_2$CH$_3$), 2.35 (t, 4H, J=7.6 Hz, CH$_2$C=), 1.44–1.24 (m, 48H), 0.87 (t, 6H, J=7.3 Hz) and $^{13}$C NMR (75.5 MHz, CDCl$_3$): δ 169.39, 137.29, 51.74, 31.93, 31.68, 29.69, 29.53, 29.42, 29.38, 29.35, 29.32, 28.61, 22.69, 14.13.

Synthesis of trans-2,3-ditetradecyll-2-butene-1,4-diol

DIBAH (15 mmol, 15 mL of 1 M solution) in hexane is added to a trans-2,3-ditetradecyl-methyl-2-butenedioate (3.33 mmol) in hexane at 0° C. and the reaction mixture is stirred for 1 h. The reaction mixture is quenched with 1 M HCl solution and stirred for 30 min. The aqueous layer is extracted with chloroform. The combined organic layers were washed with dil. HCl solution and brine, and then dried over anhydrous magnesium sulfate. Solvents are evaporated under vacuum. The reaction afforded trans-2,3-ditetradecyl-2-butene-1,4-diol in 92% yield. $^1$H NMR (300 MHz, CDCl$_3$): δ 4.12 (s, 4H, CH$_2$O, 2.21 (t, 4H, J=7.7 Hz, CH$_2$C=), 1.44–1.24 (m), 0.88 (t, 6H, J=7.3 Hz). $^{13}$C NMR (75.5 MHz, CDCl$_3$): δ 137.27, 61.71, 31.93, 30.03, 29.98. 29.90, 29.86, 29.80, 29.75, 29.68, 29.54, 29.46, 29.36, 29.25, 22.69, 14.14.

Synthesis of trans-2,3-ditetradecyl-2-butene-1,4-dimesylate

A solution of diol (3.2 mmol) and triethylamine (7 mmol) in tetrahydrofuran was prepared. To the stirred mixture, 7 mmol of methanesulfonyl chloride was added dropwise over 5 min. After the addition was complete, stirring was continued for 2 h. Cold water was poured into the reaction mixture to destroy any excess methanesulfonyl chloride. The aqueous layer was separated from the organic layer, and was extracted with diethyl ether. The organic phases were combined and washed with dilute HCl, H$_2$O, NaHCO$_3$, and H$_2$O. The organic layer was dried over MgSO$_4$ and the solvent was removed under vacuum. The reaction affored trans-2,3-ditetradecyl-2-butene-1,4-dimesylate in 99% yield. $^1$H NMR (300 MHz, CDCl$_3$): δ 4.77 (s., 4H, CH$_2$O). 3.02 (s, 6H, OMs), 2.25 (t, 4H, J=7.5 Hz, CH$_2$C=), 1.44–1.25 (m), 0.88 (t, 6H, J=7.3 Hz). $^{13}$C NMR (75.5 MHz, CDCl$_3$): δ 135.41, 67.26, 37.97, 31.91, 30.15, 29.80, 29.68, 29.60, 29.52, 29.47, 29.33, 29.21, 22.71, 14.13.

Synthesis of trans-2,3-ditetradecyl-2-butene-1,4-dithioacetate

Potassium thioacetate (6 mmol) was dissolved in 10 mL absolute ethanol under argon. To the stirred solution, dimesylate (2.15 mmol) was added dropwise over 5 min. The reaction mixture was heated to reflux for 12 h under argon and then the organic phases were combined with H$_2$O. The mixture was extracted with diethyl ether and the organic phases were washed with H$_2$O and then dried over MgSO$_4$.

The crude product was purified by column chromatography on silica gel (hexane/ether=99/1) affording trans-2,3-ditetradecyl-2-butene-1,4-dithioacetate in 87% yield. $^1$H NMR (300 MHz, CDCl$_3$): δ 3.60 (s, 4H, CH$_2$S), 2.33 (s, 6H, SAc), 2.02 (t, 4H, J=7.5 Hz, CH$_2$C=), 1.44–1.24 (m), 0.88 (t, 6H, J=7.3 Hz).

Synthesis of trans-2,3-ditetradecyl-2-butene-1,4-dithiol

The trans-2,3-ditetradecyl-2-butene-1,4-dithioacetate (0.015 mol) and 20 mL absolute ethanol (degassed by bubbling with argon) were placed in a 100 mL flask under argon. To the solution, 40 ml conc HCl were added, and the stirred mixture heated at 50° C. for 24 h. The reaction mixture was concentrated in vacuo, and the resultant oil was suspended in 20 mL H$_2$O and extracted with Et$_2$O. The extracts were washed with brine and dried over MgSO$_4$ and evaporated to dryness. The crude products were purified by column chromatography on silica gel (hexane/ethyl acetate= 1/0, 50/1) affording trans-2,3-ditetradecyl-2-butene-1,4-dithiol in 80% yield. $^1$H NMR (300 MHz, CDCl$_3$): δ 3.15 (d, 4H, J=8.0 Hz), 2.17 (t, 4H, J=7.7 Hz), 1.40 (t, 2H, J=8.0 Hz), 1.43–1.26(m), 0.88 (t, 6H, J=7.3 Hz).

TETRA SUBSTITUTED METHANE SURFACE MODIFYING AGENTS

Example 34

This example illustrates the general synthesis of tetra-substituted methane surface modifying agents is demonstrated for the formation of 2,2-ditetradecyl-1,3-propanedithiol following the synthetic scheme set forth in FIG. 8.

General Procedures $^1$H NMR (300 MHz) and $^{13}$C NMR (75 MHz) were obtained on a GE-300 (300 MHz) spectrometer with CDCl$_3$ as a solvent. All experiments were performed under an argon atmosphere and reagent grade tetrahydrofuran was dried by passage through activated alumna and degassed by using the Freeze-Pump-Thaw methods. HMPA was dried over calcium hydride and then transferred to the flask containing Na under argon. Distillation of HMPA was performed after 24 h to give pure and dried HMPA. DMF was distilled before use.

Synthesis of diethyl-2,2-ditetradecylmalonate

A solution of NaH (30 mmol) in THF (50 mL) and DMF (15 mL) was prepared at 0° C. under Ar. To this solution, diethyl malonate (10 mmol) was added slowly. The mixture was stirred at rt for 15 min, then bromotetradecane (30 mmol) was added and the mixture heated under reflux for 6 h. The reaction mixture was concentrated in vacuo, and the resultant oil was suspended in 50 mL H$_2$O. The mixture was extracted with pentane and pentane/ether (1:1), and the organic layers were washed with H$_2$O dried over MgSO$_4$ and evaporated to dryness. The crude products were purified by column chromatography on silica gel (hexane/diethyl ether=1/0, 10/1) affording diethyl-2,2-ditetradecylmalonate in 93% yield. $^1$H NMR (300 MHz, CDCl$_3$): δ 4.17 (q, 4H, J=8.0 Hz), 1.85 (t, 4H, J=8.3 Hz), 1.40–1.20 (m), 1.23 (t, 6H, J=8.0 Hz), 0.88 (t, 6H, J=8.0 Hz).

Synthesis of 2,2-ditetradecyl-1,3-propanediol

LAH (9.68 mmol) is added to a diethyl-2,2-ditetradecylmalonate (2.42 mmol) solution in THF at rt and the reaction mixture is heated under reflux for 2 h. The reaction mixture is quenched with 1 M HCl solution and stirred for 30 min. The aqueous layer is extracted with diethyl ether two times. The combined organic layers are washed with a dilute HCl solution and brine, and then dried over anhydrous magnesium sulfate. Solvents are evaporated under vacuum. The reaction afforded 2,2-ditetradecyl-1,3-propanediol in 91% yield $^1$H NMR (300 MHz, CDCl$_3$): δ 3.57 (s, 4H, CH$_2$O), 1.38–1.15 (m), 0.88 (t, 6H, J=8.0 Hz).

Synthesis of 2,2-ditetradecyl-1,3-propanedimesylate

A solution of diol (2.2 mmol) and triethylamine (5.5 mmol) in tetrahydrofuran is prepared. To the stirred mixture, 5.5 mmol of methanesulfonyl chloride was added dropwise over 5 min. After the addition was complete, stirring was continue for 2 h. Cold water was poured into the reaction mixture to destroy any excess methanesulfonyl chloride. The aqueous layer was separated from the organic layer, and was extracted with diethyl ether. The organic phases were combined and washed with dilute HCl, H$_2$O, NaHCO$_3$, and H$_2$O. The organic layer was dried over MgSO$_4$ and the solvent was removed by rotary evaporation. The reaction afforded products in 99% yield. $^1$H NMR (300 MHz, CDCl$_3$): δ 4.03 (s. 4H, CH$_2$O), 3.04 (s, 6H, OMs), 1.38–1.15 (m), 0.88 (t, 6H, J=7.7 Hz).

Synthesis 2,2-ditetradecyl-1,3-propaneditiol

Potassium thioacetate (5.5 mmol) and dimesylate (2.2 mmol) was placed in 30 mL HMPA under argon. The reaction mixture was heated to 120° C. for 20 h under argon and then the organic phases were combined with H$_2$O. The mixture was extracted with diethyl ether and the organic phases were washed with H$_2$O three times and then dried over MgSO$_4$. The crude products were dissolved in THF. LAH (8.78 mmol) was added to the reaction mixtures in THF at rt and the reaction mixture is heated under reflux for 2 h. The reaction mixture was quenched with ethanol (flushed with argon before use) under argon and stirred for 10 min. The reaction mixture was acidified with 1 M HCl solution. The aqueous layer was extracted with diethyl ether two times. The combined organic layers were washed with dilute HCl solution and brine, and then dried over anhydrous magnesium sulfate. Solvents were evaporated under vacuum. The reaction afforded 2,2-ditetradecyll-1,3-propanedithiol in approximately 85% yield. The products usually contained about 10% of the corresponding disulfide. $^1$H NMR(300 MHz, CDCl$_3$): δ 2.52 (d, 4H, J=9.3 Hz), 1.38–1.13 (m), 1.08 (t, 2H, J=9.3 Hz), 0.88 (t, 6H, J=7.7 Hz).

Example 35

This example illustrates the general synthesis of tetra substituted methane surface modifying agents is demonstrated for the formation of $(CF_3CF_2CF_2(CH_2)_{11})_2C(CH_2SH)_2$ using the procedure of Example 34.

$(CF_3CF_2CF_2CF_2(CH_2)_{11}Br$ was reacted with diethyl malonate instead of tetradecylbromide to yield $(CF_3CF_2CF_2CF_2(CH_2)_{11})_2C(COOEt)_2$. Spectroscopic data: $^1$H NMR (300 MHz, CDCl$_3$): δ 4.17 (q, 4H, J=8.0 Hz), 2.06 (t, 4H, J=7.0 Hz), 1.88 (t, 4H, J=9.0 Hz), 1.40–1.14 (m), 1.23 (t, 6H0, J=8.0 Hz).

$(CF_3CF_2CF_2CF_2(CH_2)_{11})_2C(COOEt)_2$ was reduced by LAH as described above to yield $CF_3CF_2CF_2CF_2(CH_2)_{11})_2C(CH_2OH)_2$. Spectroscopic data: $^1$H NMR (300 MHz, CDCl$_3$): δ 3.57 (s, 4H), 2.06 (t, 4H, J=7.0 Hz), 1.63–1.54 (m), 1.40–1.18 (m).

The mesylate of $(CF_3CF_2CF_2CF_2(CH_2)_{11})_2C(CH_2OH)_2$ was prepared to yield $(CF_3CF_2CF_2CF_2(CH_2)_{11})_2C(CH_2OMs)_2$. Spectroscopic data: $^1$H NMR (300 MHz, CDCl$_3$): δ 4.03 (s, 4H), 3.03 (s, 6H), 2.06 (t 4H, J=7.0 Hz), 1.64–1.54 (m), 1.40–1.18 (m).

The mesylate of $(CF_3CF_2CF_2CF_2(CH_2)_{11})_2C(CH_2OMS)_2$ was reacted with KSAc and reduced to yield $(CF_3CF_2CF_2CF_2(CH_2)_{11})_2C(CH_2SH)_2$. Spectroscopic data: $^1$H NMR (300 MHz, CDCl$_3$): δ 2.51 (d, 4H, J=9.3 Hz), 2.02 (t, 4H, J=7.0 Hz), 1.62–1.54 (m), 1.39–1.20 (m), 1.08 (t, 2H, =9.3 Hz).

DIACETYLENE CROSSLINKABLE SURFACE MODIFYING AGENTS

Example 36

This example illustrates the synthesis of $CF_3(CF_2)_9(CH_2)_{11}C\equiv C-C\equiv(CH_2)_{10}SH$, a crosslinkable surface modifying agent.

Synthesis of $CF_3(CF_2)_9(CH_2)_{11}C-C-C\equiv CH$ 1.76 g (9.045 mmol) bistrimethylsilylbutadiyne was dissolved in 20 mL dry THF and cooled to −78° C. under argon. 6.03 ml, methyl lithium-lithiumbromide complex (1.5M in ether) was added dropwise. The mixture was allowed to warm to room temperature and stirred for 3½ h. A solution of 7.22 g (9.045 mmol) $CF_3(CF_2)_9(CH_2)_{11}I$ in 20 ml THF was added at −78° C. followed by addition of 20 ml HMPA. Stirring was continued at room temperature for 1 h. Sat. aqu. $NH_4Cl$ solution was added and the mixture was extracted five times with hexane. The combined hexane layers were washed with brine, dried with $MgSO_4$ and evaporated. The crude product was suspended in 40 ml DMF and 2 g of potassium fluoride dihydrate was added. The reaction mixture was stirred vigorously at room temperature for 1 h. 50 ml of 3N HCl was added and the mixture was extracted with hexane five times. The combined organic layers were washed with brine, $NaHCO_3$ and brine, dried with $MgSO_4$ and evaporated. The residue was purified by chromatography on silica gel with hexane as eluent. Yield: 3.15 g (48%); $^1$H-NMR (300 MHz, $CDCl_3$): δ 2.25 (t, J=7 Hz, 2H), 1.97–2.15 (m, 2H), 1.91 (s, 1H), 1.50–1.65 (m, 2H), 1.25–1.44 (m, 16H).

Synthesis of $CF_3(CF_2)_9(CH_2)_{11}C\equiv C-C\equiv C(CH_2)_{10}Br$ 3.15 g (4.36 mmol) of $CF_3(CF_2)_9(CH_2)_{11}CCCCH$ was dissolved in 30 ml THF and cooled to 0° C. in an ice bath. 1.92 ml (1.92 ml (4.8 mmol) n-BuLi (2.5M in hexane) was added and the reaction mixture was stirred at 0° C. for 1 h 6.54 g (21.8 mmol) 1,10-dibromodecane was added as solid followed by 20 mL HMPA. Stirring was continued for 1 h. A saturated $NH_4Cl$ aqueous solution was added and the mixture was extracted five times with hexane. The combined hexane layers were washed with brine, dried with $MgSO_4$ and evaporated. The crude product was purified by chromatography on silica gel with hexane as eluent. Yield: 0.67 g (16%); $^1$H-NMR (300 MHz, $CDCl_3$): δ 3.39 (t, J=7 Hz, 2H), 2.23 (t, J=7 Hz, 4H), 1.94–2.12 (m, 2H), 1.84 (quint, J=7 Hz, 2H), 1.20–1.58 (m, 32H).

Synthesis of $CF_3(CF_2)_9(CH_2)_{11}C\equiv C-C\equiv C(CH_2)_{10}SH$ 0.67 g (0.711 mmol) of $CF_3(CF_2)_9(CH_2)_{10}Br$ and 0.24 g NaSH were dissolved in 20 ml absolute ethanol and sonicated under argon at 50° C. for 6 h. The mixture was poured into 50 ml 1N HCl and extracted with hexane. The combined organic layers were washed with $NaHCO_3$ and brine, dried with $MgSO_4$ and evaporated. The product was purified by chromatography on silica gel with hexane as eluent. Yield: 0.25 g (30%); $^1$H-NMR(300 MHz, $CDCl_3$): δ 2.50 (q, J=7 Hz, 2H), 2.23 (t, J=7 Hz, 4H), 1.94–2.12 (m, 2H), 1.20–1.63 (m, 35H).

SURFACE TREATMENT REACTIONS

Example 37

This example illustrates the general treatment procedure oftreating a metallic surface with trifluoromethyl terminated alkanethiols of Formula (III) (containing a small amount ca. 10% of its corresponding disulfide of Formula (V)). Of course, this same general method can be used to form monolayer (complete or partial) on the surface of any suitable material.

A metal object having a gold surface coating was placed into a 1 millimolar solution of a trifluoro terminated alkanethiol in isooctane so that the solution completely covered the object or the surface of the object to be treated. The object was allowed to remain in the solution for about 2 h resulting in an object having a surface modified with the trifluoro terminated alkanethiol forming a partial or complete monolayer.

The above general procedure was followed for a series of trifluoro terminated alkanethiols having carbon chain lengths between 10 and 14. Once the surfaces were made, the surfaces were analyzed by the surface coverage, wettability of the surface with water and the composition of the treated surface. The coverage data were determined by ellipsometry. Ulman, A. (Ed.) *Characterization of Organic Thin Films*; Butterworth-Heinemann: Boston, to 1995. The wettability data were determined by measuring the contact angle between the treated surface and deionized water as is well known in the art. The surface compositional data were determined by using X-ray photoelectron spectroscopy (XPS).

The ellipsometric data indicated that the surface treatment was nearly complete with the thickness of the coating in A increasing with increasing number of carbon atoms in the alkanethiol. The water wettability data indicated that the treated surfaces all demonstrated about the same water wettability between about 108° and about 112°. The XPS data indicated that surface composition was between about 10 and about 20 atom % fluorine, between about 30 and about 40 atom % gold and about 45 and about 55 atom % carbon.

Example 38

This example illustrates the treatment of a metallic surface with the surface modifying agent of Example 37.

The example used the generally procedure a set forth in Example 37. The agent of Example 36 formed excellent monolayers. The monolayers had the following contact angle data in hexadecane: (1) advancing contact angle: 81° and (2) receding contact angle: 68°.

This same general surface treatment procedure can be used for any surface modifying agent of Formulas (III-VIII), intermediate of Formula (A), mixtures or combination thereof. Moreover, the surface can be patterned with one or more agents of the present invention by applying a mask to the surface, treating the exposed surface with a first agent, unmasking the masked surface and treating the untreated, exposed surface with a second agent. This technique can be modified to employ more complex masks to generate surfaces with complex patterns of agents.

Although the invention has been disclosed with reference to its preferred embodiments, from reading this description those of skill in the art may appreciate changes and modification that may be made which do not depart from the scope and spirit of the invention as described above and claimed hereafter.

REFERENCES

1. Brace, N.O. *J. Org. Chem.,* 1962, 2, 3027.
2. Brace, N.O. *J. Org. Chem.,* 1962, 27, 3033.
3. Brace, N.O.; vanElswyck, J. E. *J. Org. Chem.,* 1976, 41, 766.
4. Brace, N.O. *J. Fluorine Chem.,* 1982, 20, 3027.
5. Baum, K.; Bedford, C. D.; Hunadi, R. J. *J. Org. Chem.,* 1982, 47, 2251.
6. Fuchikami, T.; Ojima, I. *Tetrahedron Lett.* 1984, 25, 303.

7. Creary, X. *J. Org. Chem.,* 1987, 52, 5026.
8. Salvador, R. L.; Saucier, M. *Tetrahedron* 1971, 27, 1221.
9. Wagner, P. J.; Truman, R. J.; Puchalski, A. E.; Wake, R. *J. Am. Chem. Soc.* 1986, 108, 7727.
10. Ishikawa, N.; Koh, M. G., Kitazume. T.; Choi, S. K. *J. Fluorine Chem.* 1984, 24, 419.
11. Uneyama, K.; Morimoto, O.; Yamshita, F. *Tetrahedron Lett.* 1989, 30, 4821.
12. Uneyama, K.; Momota, M. *Tetrahedron Lett.* 1989, 30, 265.
13. Takeyama, Y.; Ichinose; Y.; Oshima, K.; Utimoto, K. *Tetrahedron Lett.* 1989, 30, 3139.
14. Meazza G.; Gapuzzi, L.; Picardi, P. *Synthesis* 1989, 331.
15. Burger, K.; Gaa, K.; Geith, K.; Schierlinger, C. *Synthesis* 1989, 850.
16. Kobayashi, Y.; Yamamoto, K.; Kumadaki, I. *Tetrahedron Lett.* 1979, 20, 4071.
17. Park, J. D.; Lacher, J. R. *Photochemical Synthesis of Organic Fluorine Compounds*; Institution: W.A.D.C.T.R. 56-590, Pt.II; Report No. ASTIA No. 151014.
18. Moore, L. D. *Dissertation Abstr.* 1959, 20, 96.
19. Walling, C. *Free Radicals in Solution*; J. Wiley and Sons, Inc.: New York, 1957; pp 247.
20. Roedig, A in *Houben-Weyl, Methoden der organischen Chemie*; Georg Thieme Verlag, Stuttgart, 1060; pp 653.
21. Cloux, R.; Kovats, E. S. *Synthesis* 1992, 409.
22. Vol'pin, M.;Dvolaitzky, M.; Levitin, I. *Bull. Soc. Chim. Fr.* 1970, 1526.
23. Giese, B.; Jianing, H.; Mehl, W. *Chem. Ber.* 1988, 121, 2064.
24. Ulman, A. *An Introduction to Ultrathin Organic Films*; Academic: San Diego, 1991.
25. Whitesides, G. M.; Laibinis, P. E. *Langmuir* 1990, 6, 87.

What is claimed is:

1. A composition comprising a substrate including a surface, the surface including a partial or complete monolayer of a composition comprising a surface modifying agent of Formula (VII):

$$R_f\text{—}R'''\text{—}REZ \qquad (VII)$$

where:

$R_f$ is a linear or branched fluorocarbon-containing group;

R''' is a crosslinkable group selected from the group consisting of an acetylenic group, a diacetylenic group, polyacetylenic group, an alpha amino acid group, an alpha hydroxy acid group and a dialkoxysilenyl group;

R is a carbon-containing group;

E is S; and

Z is a hydrogen atom.

2. The composition of claim 1, wherein $R_f$ is linear fluorocarbon-containing group and R is linear carbon-containing group.

3. The composition of claim 1, wherein $R_f$ is a linear fluorinated alkyl group and R is linear alkyl group.

4. The composition of claim 1, wherein $R_f$ is linear fluorinated alkyl group group, R is linear alkyl group and R''' is selected from the group consisting of diacetylenic group and a polyacetylenic group.

5. The composition of claim 1, wherein $R_f$ is a linear fluorinated alkyl group of the general formula $F(CF_2)_k(CH_2)_1$, R''' is a diacetylenic group and R is linear alkyl group of the general formula $(CH_2)_{pp}$, where k in an integer having a value between 1 and 30, 1 is an integer having a value between 0 and 2, and pp is an integer having a value between 1 and 50.

6. The composition of claim 5, wherein k is between 5 and 20 and pp is between 1 and 40.

7. The composition of claim 5, wherein k is between 8 and 18 and pp is between 1 and 40.

8. A composition comprising a substrate including a surface, the surface including a partial or complete monolayer of a surface modifying agent of Formula (VII):

$$R_f\text{—}R'''\text{—}REZ \qquad (VII)$$

where:

$R_f$ is a linear fluorocarbon-containing group;

R''' is a crosslinkable group selected from the group consisting of an acetylenic group, a diacetylenic group, polyacetylenic group, an alpha amino acid group, an alpha hydroxy acid group and a dialkoxysilenyl group;

R is a carbon-containing group; and

EZ is SH.

9. The composition of claim 8, wherein R is linear carbon-containing.

10. The composition of claim 8, wherein $R_f$ is a linear fluorinated alkyl group and R is linear alkyl group.

11. The composition of claim 8, wherein $R_f$ is a linear fluorinated alkyl group, R is linear alkyl group and R''' is selected from the group consisting of a diacetylenic group and a polyacetylenic group.

12. The composition of claim 8, wherein $R_f$ is a linear fluorinated alkyl group of the general formula $F(CF_2)_k(CH_2)_1$ and R is linear of the general formula $(CH_2)_{pp}$, where k in an integer having a value between 1 and 30, 1 is an integer having a value between 0 and 2 and pp is an integer having a value between 1 and 50.

13. The composition of claim 12, wherein k is between 5 and 20 and pp is between 1 and 40.

14. The composition of claim 12, wherein k is between 8 and 18 and pp is between 1 and 40.

15. A composition comprising a substrate including a surface, the surface including a partial or complete monolayer of a surface modifying agent of Formula (VIIa):

$$R_f\text{—}C\equiv C\text{—}C\equiv C\text{—}REH \qquad (VIIa)$$

where:

$R_f$ is a linear or branched fluorocarbon-containing group;

R is a carbon-containing group;

EH is SH.

16. The composition of claim 15, wherein $R_f$ is a linear fluorocarbon-containing group and R is linear carbon-containing.

17. The composition of claim 15, wherein $R_f$ is a linear fluorinated alkyl group and R is linear alkyl group.

18. The composition of claim 17, wherein $R_f$ is a fluorinated linear alkyl groups having the general formula $F(CF_2)_k(CH_2)_1$ and R is a linear alkyl group of the general formula $(CH_2)_{pp}$, where k in an integer having a value between 1 and 30, 1 is an integer having a value between 0 and 2 and pp is an integer having a value between 1 and 50.

19. The composition of claim 18, wherein k is between 5 and 20 and pp is between 1 and 40.

20. The composition of claim 18, wherein k is between 8 and 18 and pp is between 1 and 40.

* * * * *